United States Patent
Choi et al.

(10) Patent No.: US 7,455,756 B2
(45) Date of Patent: Nov. 25, 2008

(54) BIOSENSOR

(75) Inventors: Moon-Hee Choi, Kyonggi (KR); Gang Cui, Jilin (CN); Jae-Hyun Yoo, Seoul (KR); Ho-Choll Cho, Seoul (KR); Min-Sun Kim, Seoul (KR); Fenghua Zhang, Jilin (CN); Hakhyun Nam, Seoul (KR); Geun-Sig Cha, Seoul (KR)

(73) Assignee: i-SENS, Inc., Seoul (KR)

( * ) Notice: Subject to any disclaimer, the term of this patent is extended or adjusted under 35 U.S.C. 154(b) by 785 days.

(21) Appl. No.: 10/476,634

(22) PCT Filed: May 30, 2002

(86) PCT No.: PCT/KR02/01023

§ 371 (c)(1),
(2), (4) Date: Oct. 31, 2003

(87) PCT Pub. No.: WO02/097416

PCT Pub. Date: Dec. 5, 2002

(65) Prior Publication Data

US 2004/0140209 A1     Jul. 22, 2004

(30) Foreign Application Priority Data

May 30, 2001 (KR) ............... 2001-30169
Jul. 28, 2001 (KR) ............... 2001-45720

(51) Int. Cl.
*G01N 27/327* (2006.01)

(52) U.S. Cl. ............... 204/403.01; 204/403.14

(58) Field of Classification Search ............... 204/403.01–403.15
See application file for complete search history.

(56) References Cited

U.S. PATENT DOCUMENTS

| | | | |
|---|---|---|---|
| 5,063,081 A | | 11/1991 | Cozzette et al. |
| 5,723,345 A | * | 3/1998 | Yamauchi et al. ............ 436/518 |
| 5,830,680 A | | 11/1998 | Meyerhoff et al. |
| 5,863,400 A | * | 1/1999 | Drummond et al. ......... 205/778 |
| 6,153,069 A | * | 11/2000 | Pottgen et al. ......... 204/403.11 |
| 6,299,757 B1 | * | 10/2001 | Feldman et al. ............. 205/775 |
| 6,696,240 B1 | * | 2/2004 | Kloepfer et al. ............... 435/4 |
| 7,045,046 B2 | * | 5/2006 | Chambers et al. ........... 204/400 |

FOREIGN PATENT DOCUMENTS

| | | |
|---|---|---|
| JP | 9-21778 | 1/1997 |
| JP | 9-101280 | 4/1997 |
| JP | 10-0349000 | 8/2002 |

* cited by examiner

*Primary Examiner*—Alex Noguerola
(74) *Attorney, Agent, or Firm*—Bachman & LaPointe, P.C.

(57) ABSTRACT

A biosensor, for use in measurement of an analyte, includes a microporous membrane support, a first electrode system, a second electrode system, and a pair of insulating films. The first electrode system is formed on the surface of the microporous membrane support and the second electrode system is formed on the opposite surface of the microporous membrane support. The biosensor enables a rapid, simple, separation-free, and selective detection of the analytes. The biosensor does not require any bulky additional electrode, so that miniaturization, point-of-car testing, and disposability can be achieved.

13 Claims, 23 Drawing Sheets

BIOSENSOR

This application is a 371 of PCT/KR02/01023, filed on May 30, 2002, which claims priority from Republic of Korea application 2001-30169, filed on May 30, 2001, and Republic of Korea application 2001-45720, filed on Jul. 28, 2001.

FIELD OF THE INVENTION

The present invention relates to a biosensor, and more particularly, to a biosensor comprising a microporous membrane support, a first electrode system, a second electrode system, and a pair of insulating films, wherein the first electrode system is formed on the surface of the microporous membrane support and the second electrode system is formed on the opposite surface of the microporous membrane support.

BACKGROUND OF THE INVENTION

A biosensor is a device, probe, or electrode which, when in contact with an appropriate sample, produces an electrical signal in the presence of the desired analyte. The biosensor is normally constructed by immobilizing a biologically sensitive material in intimate contact with a suitable transducing system to convert the concentration of the analyte into a quantifiable signal.

In spite of several advantages, the currently available biosensors all suffer from many problems awaiting solution: chemical interference, environmental effects, long-term stability, signal-to-noise ratio and design of the sensor's packaging system.

The following trends are recognizable in the development of biosensors:

a) Miniaturization b) Determination of several reagents with an array sensor system combining more than one sensing element c) Development of mass producible disposable sensors d) In vivo analysis using implantable biochips e) Processing of the output from an arrayed sensor system of with an artificial intelligence system Meanwhile, the development of a rapid, simple, separation-free method for the detection of proteins has been a long-standing goal. Chromogenic and fluorogenic galactoside-dextran substrates have been used to devise homogeneous enzyme immunoassays (EIAs) for C-reactive protein, ferritin, and immunoglobulins (Gibbons et al., "Homogeneous Enzyme Immunoassay for Proteins Employing β-Galactosidase," Analytical Biochemistry 102/167-170, 1980; and Armenta et al., "Improved Sensitivity in Homogeneous Enzyme Immunoassays Using a Fluorogenic Macromolecular Substrate: An Assay for Serum Ferritin," Analytical Biochemistry 146/211-219, 1985). However, the low degree of modulating enzyme activity in this homogeneous protocol has rendered the method impractical for real world applications.

Also, a separation-free dual solid-phase EIA for macromolecules, which relies on the partitioning of an enzyme conjugate (biotin-glucose-6-phosphate dehydrogenase-antibody) between two solid phases of polystyrene latex-bound avidin and polystyrene latex-bound analyte, has been reported (Schray et al., "Separation-Free Dual Solid Phase Enzyme Immunoassay for Macromolecules," Analytical Chemistry, 60/353-56 1988). However, this assay scheme requires 24 hours for enzymatic generation of a detectable product.

It has long been recognized that coupling electrochemical detection with EIAs would be advantageous. Electrodes are insensitive to the color or turbidity of a test sample and can therefore be used to develop methods directly applicable to whole blood samples. However, most of the many reports regarding the use of electrochemical detection to devise EIAs or "immunosensors" have relied on using such sensors as solid phases in heterogeneous assay arrangements in which antibodies are immobilized at the surface of a given electrode. After incubation of a sample with other reagents, the surface of the electrodes has to be washed before adding the substrate needed to measure bound enzyme activity.

As a specific example, in U.S. Pat. No. 5,063,081 issued Nov. 5, 1991, Cozzette et al. disclose a ligand/ligand receptor-based biosensor for detecting a particular analyte species, such as an antigen. Here, a base sensor, comprising a catalytic indicator electrode using a noble late transition metal such as iridium, gold, platinum, or silver, is surrounded by a combined reference and counter electrode made of, for example, silver and silver chloride (columns 25-26). An antibody is immobilized on the base sensor. The resulting biosensor is then brought into contact with a mixture comprising the sample and a second analyte-specific antibody, which is labeled (columns 45-46). A permselective silane layer may also be used as a screen against interfering species. However, unbound materials and interfering electroactive species are preferably removed from the sensor by using either a wash solution or by using the solution containing the enzyme substrate as a wash (columns 47-49).

As another specific example, in U.S. Pat. No. 5,830,680 issued Nov. 3, 1998, Meyerhoff et al. disclose an enzyme sandwich immunoassay cassette for detecting an analytical signal over any background signal originating from a bulk solution in contact with the cassette. Here, the cassette comprises a microporous membrane support having coated on one side thereof a conductive metal layer and at least a first capture antibody layer immobilized over the conductive metal layer in at least a first spatially distinct area of the microporous membrane support. Referring to FIG. 1, which is a diagram of a diffusion cell arrangement, it can be seen that the cassette requires an additional auxiliary electrode and/or a reference electrode, such that miniaturization and point-of-care testing are not achieved.

Therefore, despite all of the past and current research activity in this area, a new biosensor that avoids the above-described disadvantages has long been desired.

SUMMARY OF THE INVENTION

An object of the present invention is to provide a biosensor comprising a microporous membrane support; a first electrode system consisting of a working electrode on which biologically active materials are immobilized, a first electrode connector, and a first lead outlet; a second electrode system consisting of a counter electrode, a second electrode connector and a second lead outlet; a pair of insulating films, covering surfaces of the first and second electrode systems except for the areas of the working electrode, the first electrode connector, the counter electrode and the second electrode connector; wherein, the first electrode system is formed on the surface of the microporous membrane support and the second electrode system is formed on the opposite surface of the microporous membrane support, wherein, the working electrode and the counter electrode are formed directly on the microporous membrane support, whereby the electrodes being microporous and allowing a sample to pass through the surface of the working electrode to the surface of the counter electrode.

A further object of the present invention is to provide a biosensor comprising a microporous membrane support, a first electrode system on which a biologically active material is immobilized, a second electrode system, a pair of insulating films, a pad, and a pair of covers having a hole, wherein the first electrode system is formed on the surface of the microporous membrane support, the second electrode system is formed on the opposite surface of the microporous membrane support, and an enzyme-analyte conjugate or an enzyme-antibody conjugate is immobilized on the pad.

BRIEF DESCRIPTION OF THE DRAWINGS

The application of the preferred embodiments of the present invention is best understood with reference to the accompanying drawings, in which like reference numerals are used for like and corresponding parts, wherein.

DETAILED DESCRIPTION OF THE INVENTION

The present invention relates to a biosensor comprising a microporous membrane support, a first electrode system, a second electrode system, and a pair of insulating films (or a pair of insulating substrates with electrical connectors), wherein the first electrode system is formed on the surface of the microporous membrane support and the second electrode system is formed on the opposite surface of the microporous membrane support. The biosensor according to the present invention does not require any additional electrode.

Figure 1:
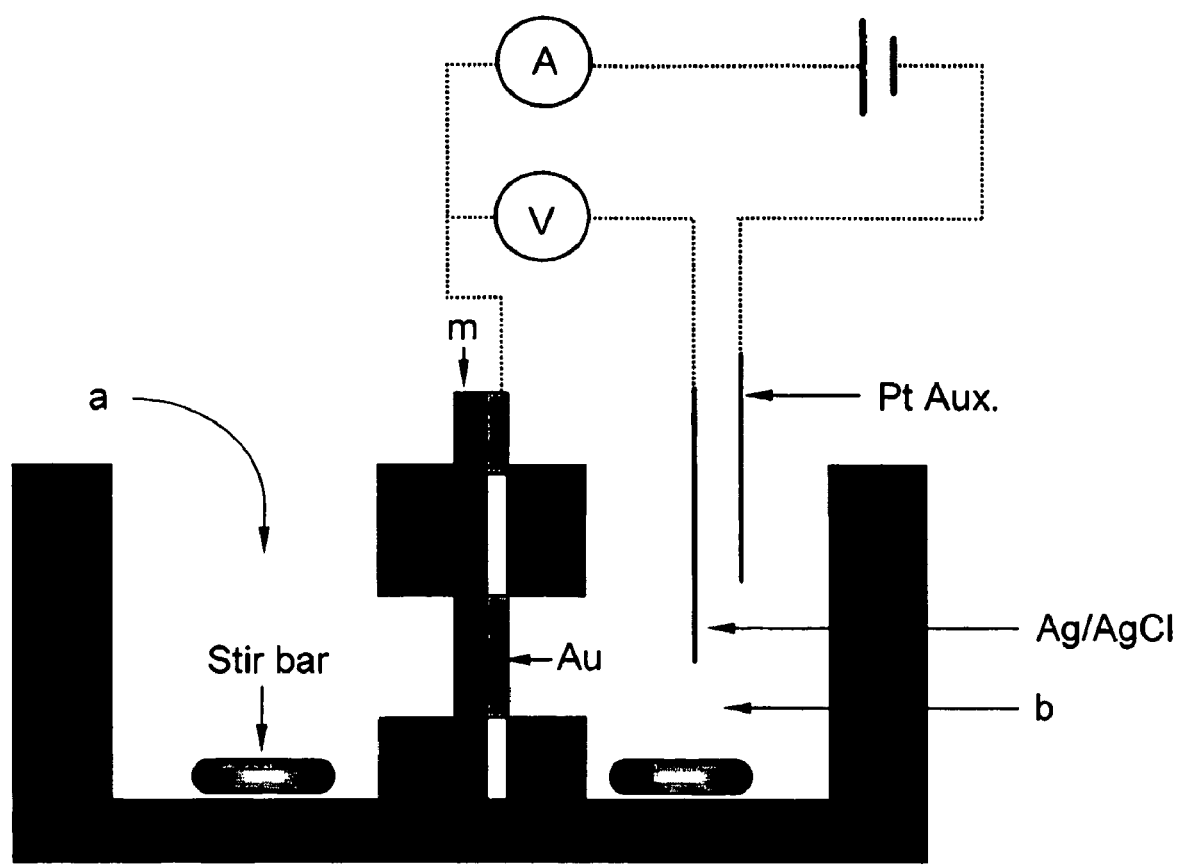
FIG. 1 is a schematic diagram of a diffusion cell arrangement of the prior art, in which only one electrode system is formed on a microporous membrane support;
a: an analyte solution b: a substrate solution
Figure 2A:
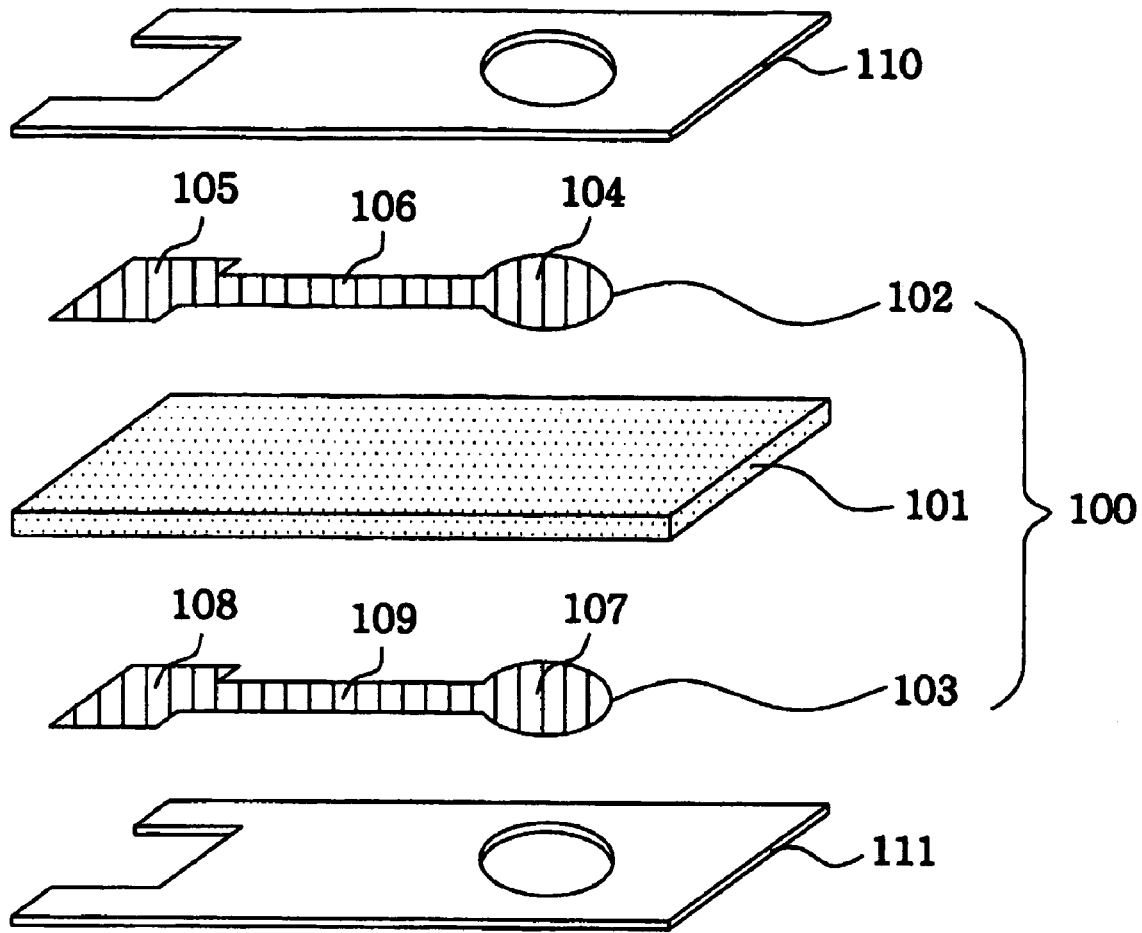
FIG. 2a is an exploded perspective view of a symmetric microporous electrode-based biosensor formed on one whole strip in accordance with a first embodiment of the present invention.
Figure 2B:
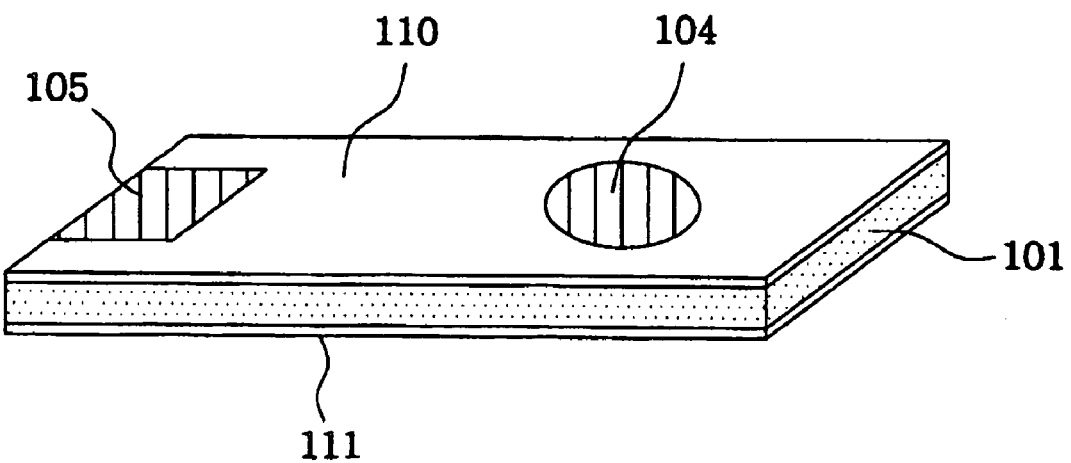
FIG. 2b is a perspective view of the biosensor of the first embodiment of the present invention.
Figure 2C:
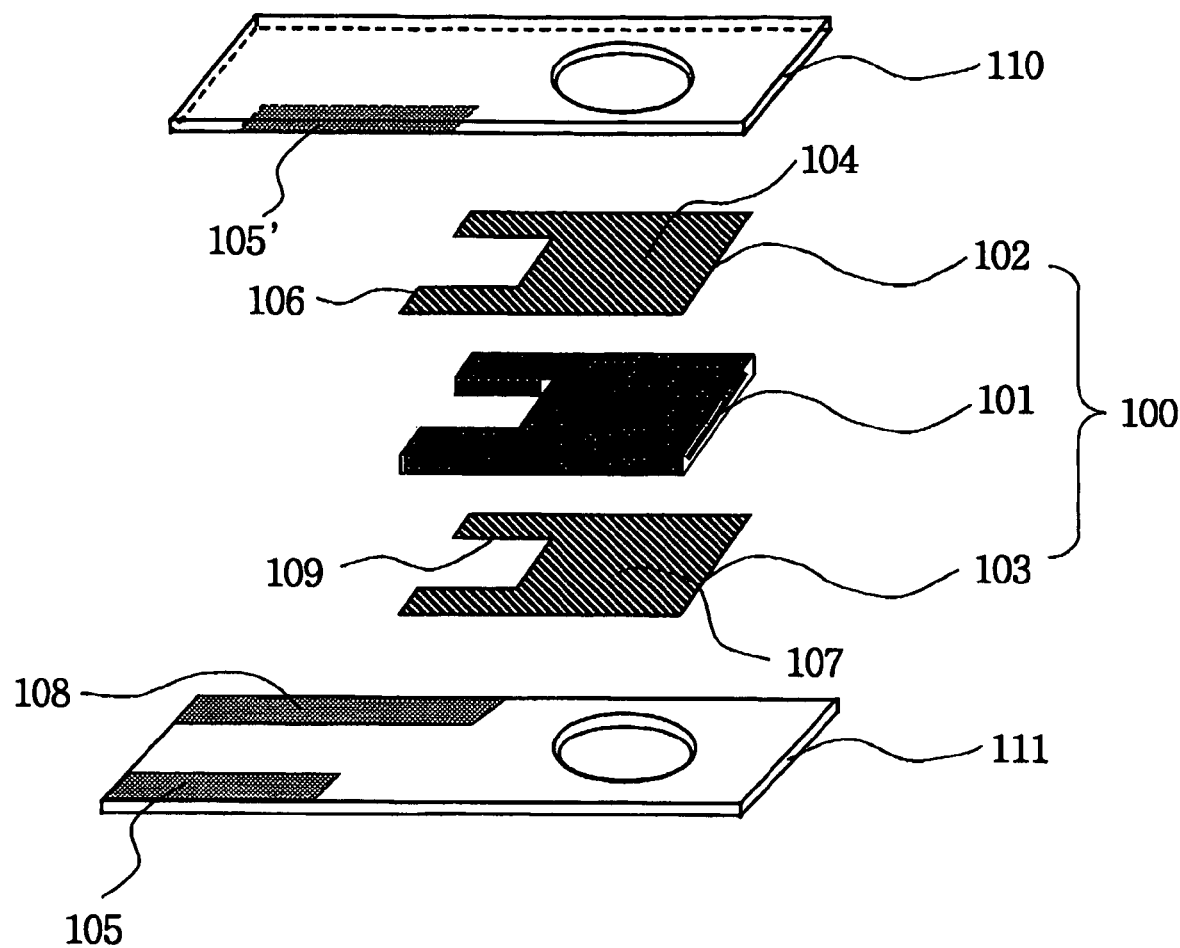
FIG. 2c is an exploded perspective view of a symmetric microporous electrode-based biosensor, in which modification of the biosensor, with electrical connectors separately formed on two insulating substrates in accordance with a first embodiment of the present invention.
Figure 2D:
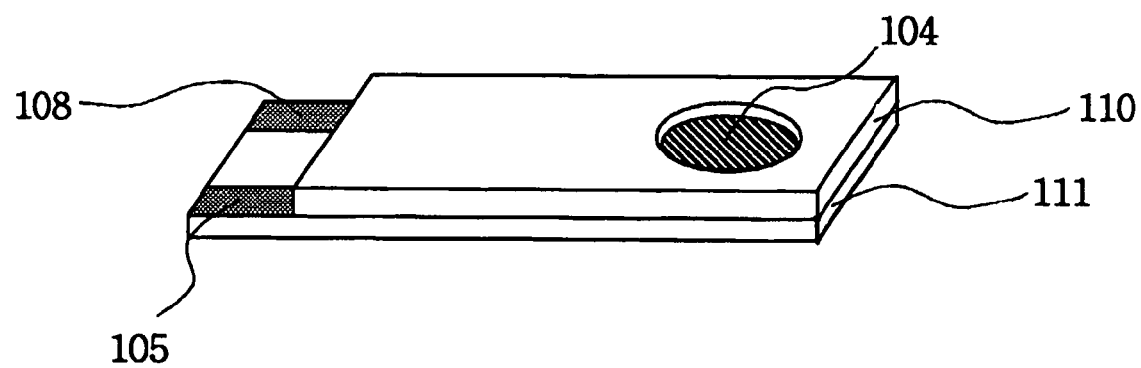
FIG. 2d is a perspective view of the biosensor of 2c, in which modification of the biosensor, in accordance with a first embodiment of the present invention.

Referring to FIGS. 2a and 2b, an electrochemical cell (100) used in the biosensor according to the present invention comprises a microporous membrane support (101), a first electrode system (102), and a second electrode system (103). The first electrode system (102) consists of a working electrode (104) on which a biologically active material is immobilized, a first electrode connector (105), and a first lead outlet (106). The second electrode system consists of a counter electrode (107), a second electrode connector (108), and a second lead outlet (109). The first and second electrode systems (102, 103) are electrically connected by the connection of the electrode connectors (105, 108), via, for example, alligator clips or solder.

Referring to FIGS. 2c to 2f, in which modification of the biosensor of 2a, the electrochemical cell (100) used in the biosensor according to the present invention comprises a microporous membrane support (101), a first electrode system (102), and a second electrode system (103). The first electrode system (102) consists of a working electrode (104) on which a biologically active material is immobilized, a first electrode connector (105) formed on the lower side of the top insulating film, and a first lead outlet (106). The second electrode system consists of a counter electrode (107), a second electrode connector (108) formed on the upper surface of the bottom insulating film, and a second lead outlet (109). The counter electrode (107) is symmetrical (FIG. 2c) or asymmetrical (FIG. 2e) to the working electrode (104). The first and second lead outlets (106 and 109) are press connected to the first and second electrode connectors (105 and 108), and the segmented first connector (105') formed on the lower side of top film and the first electrode connector 105 formed on the surface of bottom film are also press connected to arrange the two connectors (105' and 105) in face-up direction on bottom substrate. The first and second electrode systems (102, 103) are electrically connected by the connection of the electrode connectors (105, 108) by inserting them into a socket.

The first and second electrode systems (102, 103) are usually formed by sputtering electrically conductive material through chemical vapor deposition or physical vapor deposition or by screen-printing an electrically conductive material. Examples of the electrically conductive material that can be used to form the first and second electrode systems (102, 103) include, but are not limited to, conductive polymer, carbon, and an conductive metal such as gold, platinum, silver, rhodium, iridium, ruthenium, palladium, osmium, or copper. The electrically conductive material is formed in a layer that usually varies in thickness from about 150 Å to about 1000 Å. More preferably, the conductive layer is 200-800 Å thick. Most preferably, the conductive layer is 300-600 Å thick.

Materials that can be used to form the microporous membrane support (101) should be compatible with organic solvents frequently used in immobilizing a biologically active material such as an enzyme, an electron transfer mediator, and an antibody on the electrode system and should exhibit a sufficiently high tensile strength to resist tearing and/or other distortions in the porous structure during manipulation. Examples of the material that can be used to form the microporous membrane support (101) include an organic polymer (e.g., nylon, nitrocellulose, polyvinylidene difluoride, polysulfone, polyester, or polycarbonate) and an inorganic material such as a porous ceramic or an absorptive ceramic. A microporous nylon mesh is preferred because it is naturally hydrophilic and is commercially available in a form that is substantially free of wetting agents.

Even after the membrane has been coated with the conductive layer, it could be still microporous, having pore sizes within the general range of about 0.01 microns to about ten microns. Even larger pore sizes are theoretically possible, being limited only by the expense of additional conductive material being used to partially occlude the pore. A preferred average pore size is from about 0.2 µm to about 0.45 µm. This pore size enables analytes as well as substrates having molecular weight of no more than 5000 Da to pass through the pores.

The surfaces of the electrochemical cell (100) are covered with insulating films (110, 111), excluding the areas of the working electrode (104), the first electrode connector (105), the counter electrode (107) and the second electrode connector (108). Material that can be used to form the insulating films (110, 111) include, but are not limited to, polyvinyl chloride (PVC) or its copolymer such as polyvinyl chloride-bis(2-ethylhexyl)sebacate, polyethylene, polyurethane, polycarbonate, polyester, etc. The insulating films (110, 111) can also be formed by screen-printing an insulating polymer paste on the nylon membrane, followed by heat treatment. The insulating films (110, 111) should limit the diffusion of substrate through the area of the microporous membrane only and should minimize the distortion of the biosensor. If the size of microporous electrode and nylon membrane is same as shown in FIGS. 2c to 2f, electrical connections may be printed separately on the insulating films and pressed to connect electrodes and assemble the biosensor system.

This format of biosensors (2c-2f) has an advantage in mass fabrication; the gold-deposited microporous electrode and the connecting electrodes printed on insulating covers can be prepared separately and assembled as a whole in one process after immobilizing the biomaterial on the working electrode. The asymmetric double-sided electrode (2e and 2f) may be easier to prepare than the symmetric double-sided electrode (2c and 2d) if plasma deposition methods are used; the asymmetric double-sided electrode may require one time deposition of the electrode on the opposite side of the screen-printed counter electrode, while the symmetric double-sided electrode require to deposit the electrodes twice after breaking the vacuum.

The biosensor according to the present invention enables the rapid, simple, and separation-free electrochemical immunoassay, and selective detection of the analyte. In addition, the biosensor does not require any additional electrode such that miniaturization, point-of-care-testing, and disposability can be achieved.

Figure 3:
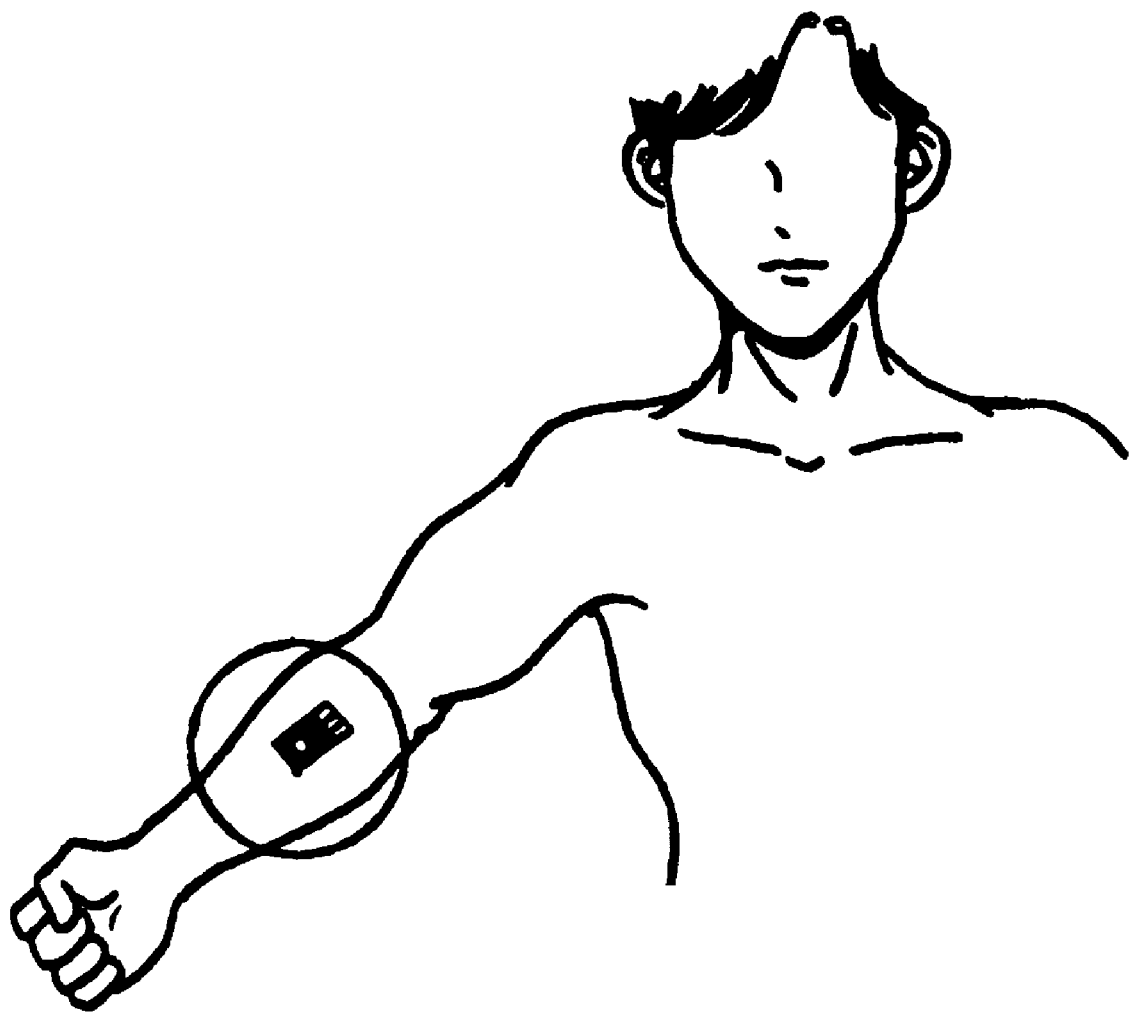
FIG. 3 is a diagram illustrating an example of an application of the biosensor, in accordance with the first embodiment of the present invention.

As shown in FIG. 3, the biosensor according to the present invention can be directly applied to a human body for the detection of a variety of samples, including biomaterials. Biomaterials to be detected include metabolites, e.g., glucose, cholesterol, lactate, creatinine, proteins, hydrogen peroxide, alcohols, amino acids, glutamate pyruvate, and glutamate oxaloacetate. For instance, cholesterol, lactate, glutamate, hydrogen peroxide, and alcohol can be quantitatively analyzed using cholesterol oxidase, lactate oxidase, glutamate oxidase, horseradish peroxidase, or alcohol oxidase, respectively. The electron transfer mediator provided for the working electrode may employ ferrocene or its derivatives, quinone or its derivatives, organic conducting salts, or viologen. An electron transfer mediator may be immobilized on the working electrode in combination with the enzyme, and a mixed-valence compound capable of forming redox couples is preferred. Preferred compounds include hexaamineruthenium (III) chloride, potassium ferricyanide, potassium ferrocyanide, dimethylferrocene, ferricinium, ferocene-monocarboxylic acid, 7,7,8,8-tetracyanoquinodimethane, tetrathiafulvalene, nickelocene, N-methylacidinium, tetrathiatetracene, N-methylphenazinium, hydroquinone, 3-dimethylaminobenzoic acid, 3-methyl-2-benzothiozolinone hydrazone, 2-methoxy-4-allylphenol, 4-aminoantipyrin, dimethylaniline, 4-aminoantipyrene, 4-methoxynaphthol, 3,3,5,5-tetramethylbenzidine, 2,2-azino-d-[3-ethylbenzthiazoline sulfonate], o-dianisidine, o-toluidine, 2,4-dichloro phenol, 4-aminophenazone, benzidine, and Prussian blue.

Figure 4A:
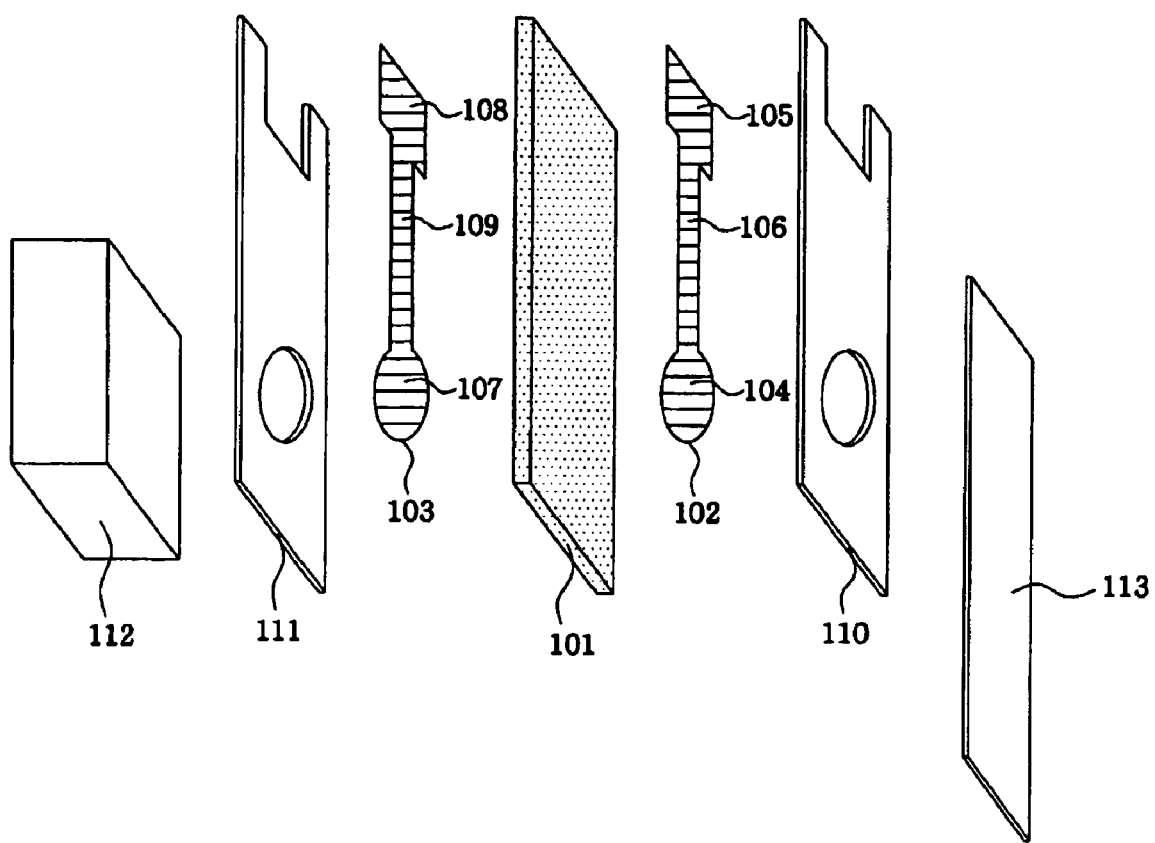
FIG. 4a is an exploded perspective view of a biosensor in accordance with a second embodiment of the present invention.
Figure 4B:
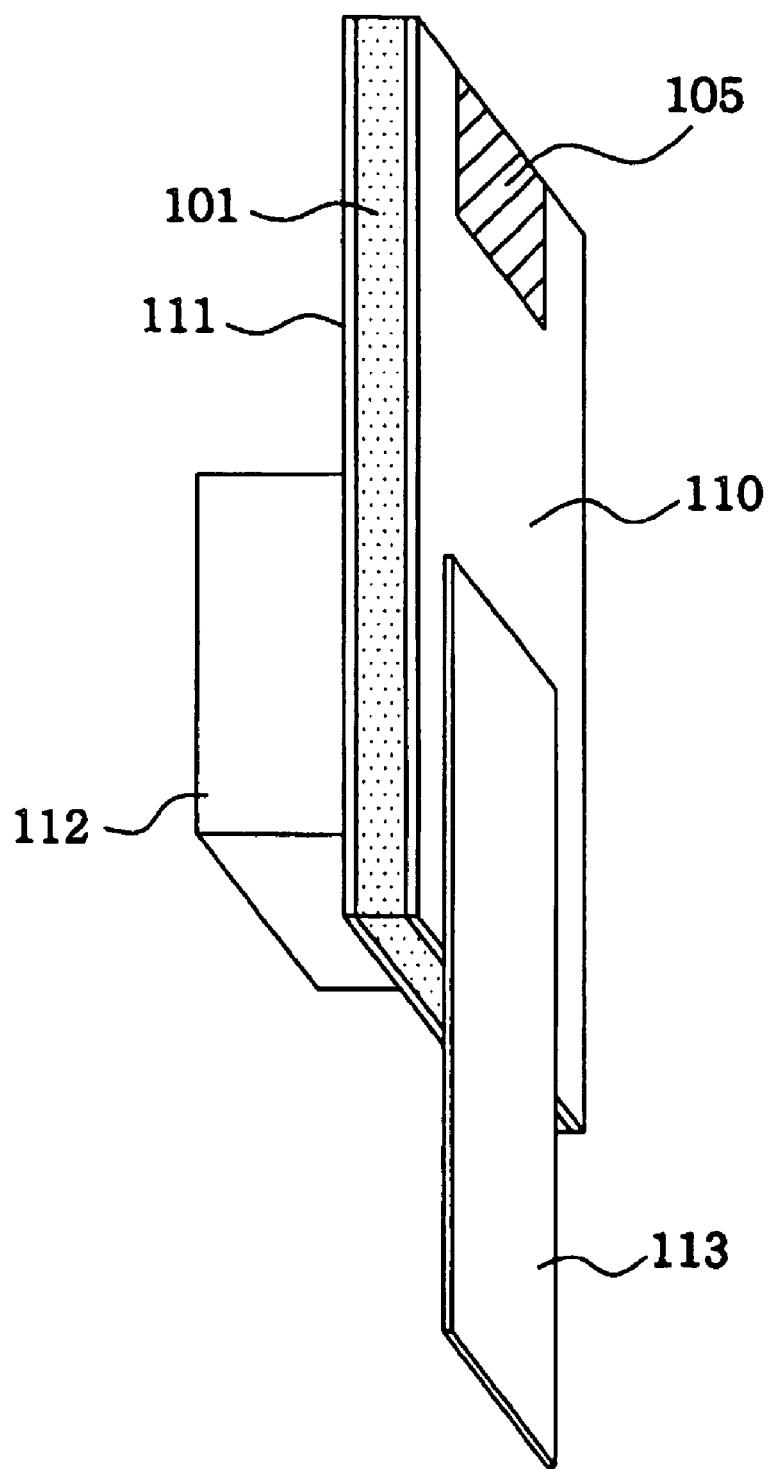
FIG. 4b is a perspective view of a biosensor in accordance with the second embodiment of the present invention.

Another preferred embodiment of the biosensor according to the present invention is shown in FIGS. 4a and 4b, wherein the biosensor comprises: a microporous membrane support (101); a first electrode system (102) consisting of a working electrode (104) on which a biologically active material is immobilized, a first electrode connector (105) and a first lead outlet (106); a second electrode system (103) consisting of a counter electrode (107), a second electrode connector (108) and a second lead outlet (109); a pair of insulating films (110, 111); an absorption pad (112); and a thin film made of porous material (113) through which an analyte is introduced via capillary action.

Figure 5:
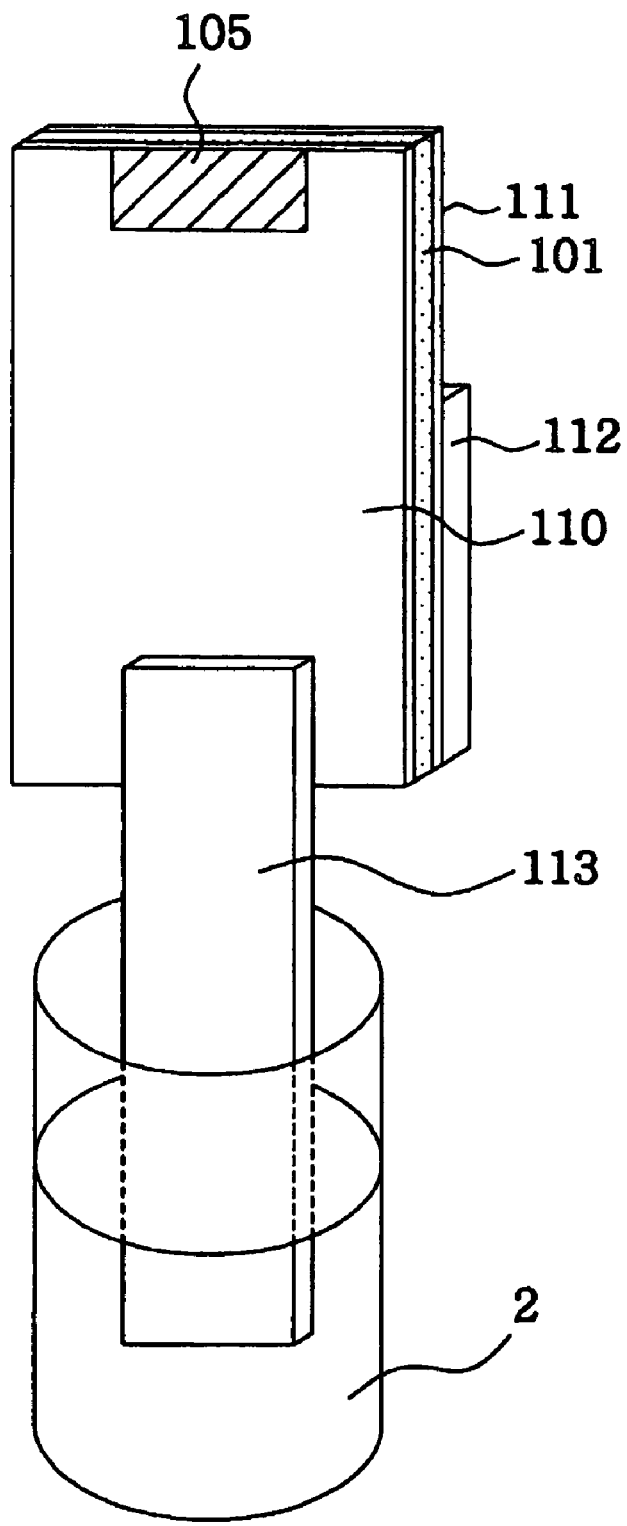
FIG. 5 is a diagram illustrating an example of an application of the biosensor, in accordance with the second embodiment of the present invention, to a sample solution.

Referring to FIGS. 4a, 4b, and 5, the working principle of the biosensor is described in more detail. A sample solution (2) containing an analyte is introduced via capillary action, through a thin porous material (113) in combination with the absorption pad (112) behind the microporous electrode. During this process, interference such as solid particles (hematocrits) contained in human blood can be eliminated by size and charge exclusion, polarity phospholipid, and mixed control such that only plasma comes into contact with the biologically active material immobilized on the working electrode (104). With the catalytic action of the biologically active material, the analyte is an electrochemically active species that generates easily oxidizable or reducible species. The redox species transfer or receive electrons at the electrode to result in electrical signal that is proportional to the concentration of the analyte and thus quantitative measurement can be achieved. In addition, with the regulation of the chemical potential produced by the action of the microporous membrane support (101), absorption pad (112), and thin porous material (113), the flow of the sample solution can be adjusted to a suitable range.

Meanwhile, the sample solution (2) introduced into the inside of the biosensor, as well as the species produced by the enzymatic reaction, are absorbed into the absorption pad (112), such that continuous measurements can be ensured for about thirty minutes to about twenty hours. This type of biosensor may be called a self-sampling-and-flowing biosensor. No mechanical components such as peristaltic pump and complicate flow channel are required to maintain a continuous flow of sample. Further, since continuous measurement is possible, the biosensor is applicable to body fluids, in addition to blood, as shown in FIG. 3.

Figure 6A:
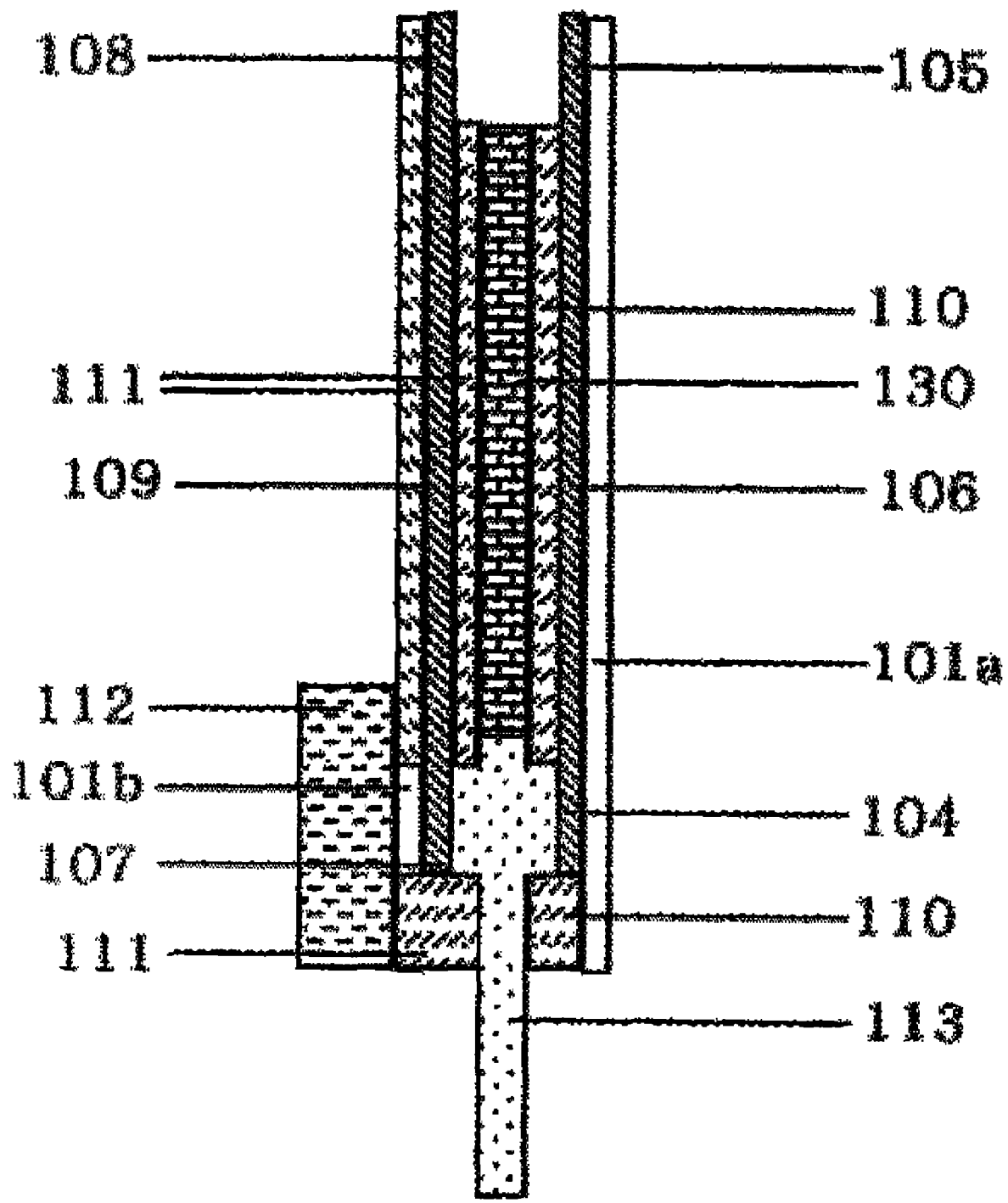
FIGS. 6a and 6b are cross sectional views of the biosensors with modified sampling capillary assembled in accordance with the second embodiment of the present invention.
Figure 6B:
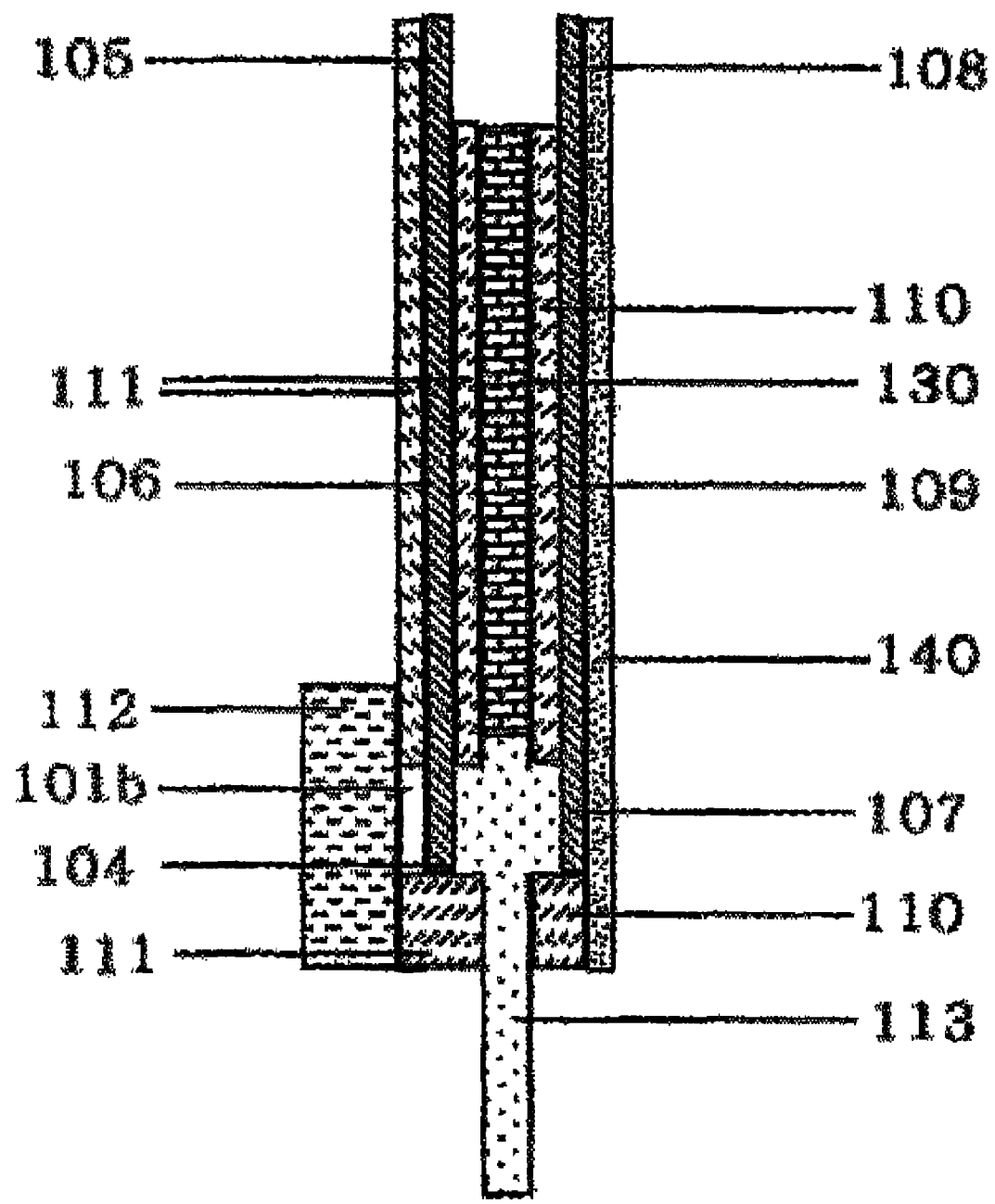

FIGS. 6a and 6b show additional embodiments of the present invention. In FIG. 6a, the biosensor further comprises first and second microporous membrane supports (101a, 101b) and an adhesive layer (130); in FIG. 6b, the biosensor further comprises the second microporous membrane support (101b), the adhesive layer (130), and a plastic substrate (140).

The biosensor according to the present invention can be also used as a separation-free solid phase immunosensor for the detection of the analyte protein by an EIA.

Figure 7A:
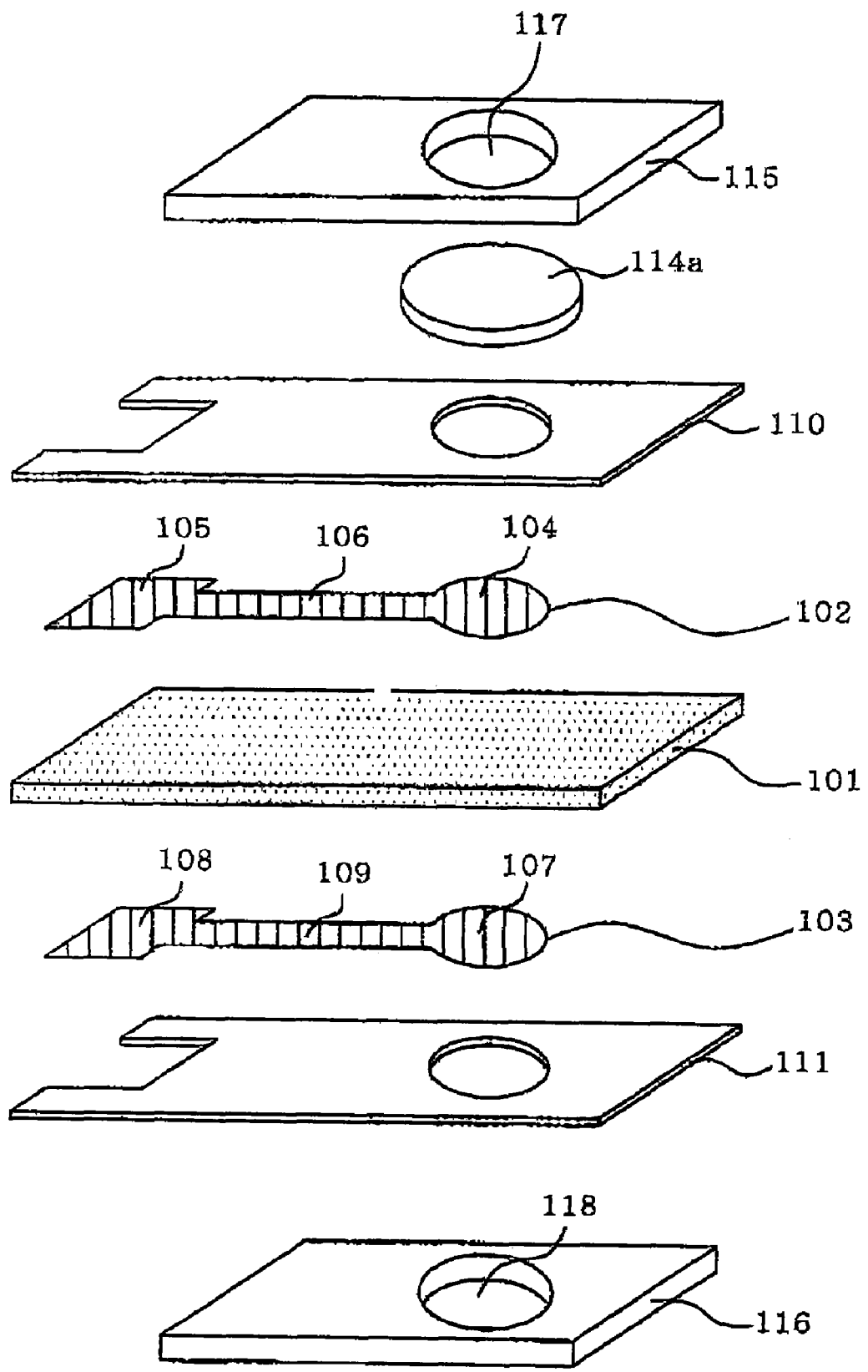
FIG. 7a is an exploded perspective view of a biosensor in accordance with a third embodiment of the present invention; [I recommend using a separate figure number with respect to FIGS. 7b-7e]

FIG. 7a shows a preferred embodiment of the biosensor according to the present invention. Referring to FIG. 7a, the biosensor for the EIA comprises: a microporous membrane support (101); a first electrode system (102) consisting of a working electrode (104) on which a biologically active material (antibody) is immobilized, a first electrode connector (105) and a first lead outlet (106); the second electrode system (103) consisting of a counter electrode (107), a second electrode connector (108) and a second lead outlet (109); a pair of insulating films (110, 111); a pad (114a) on which an enzyme-analyte conjugate is absorbed and dried; and a pair of covers (115, 116) having holes (117, 118), respectively.

Figure 8:
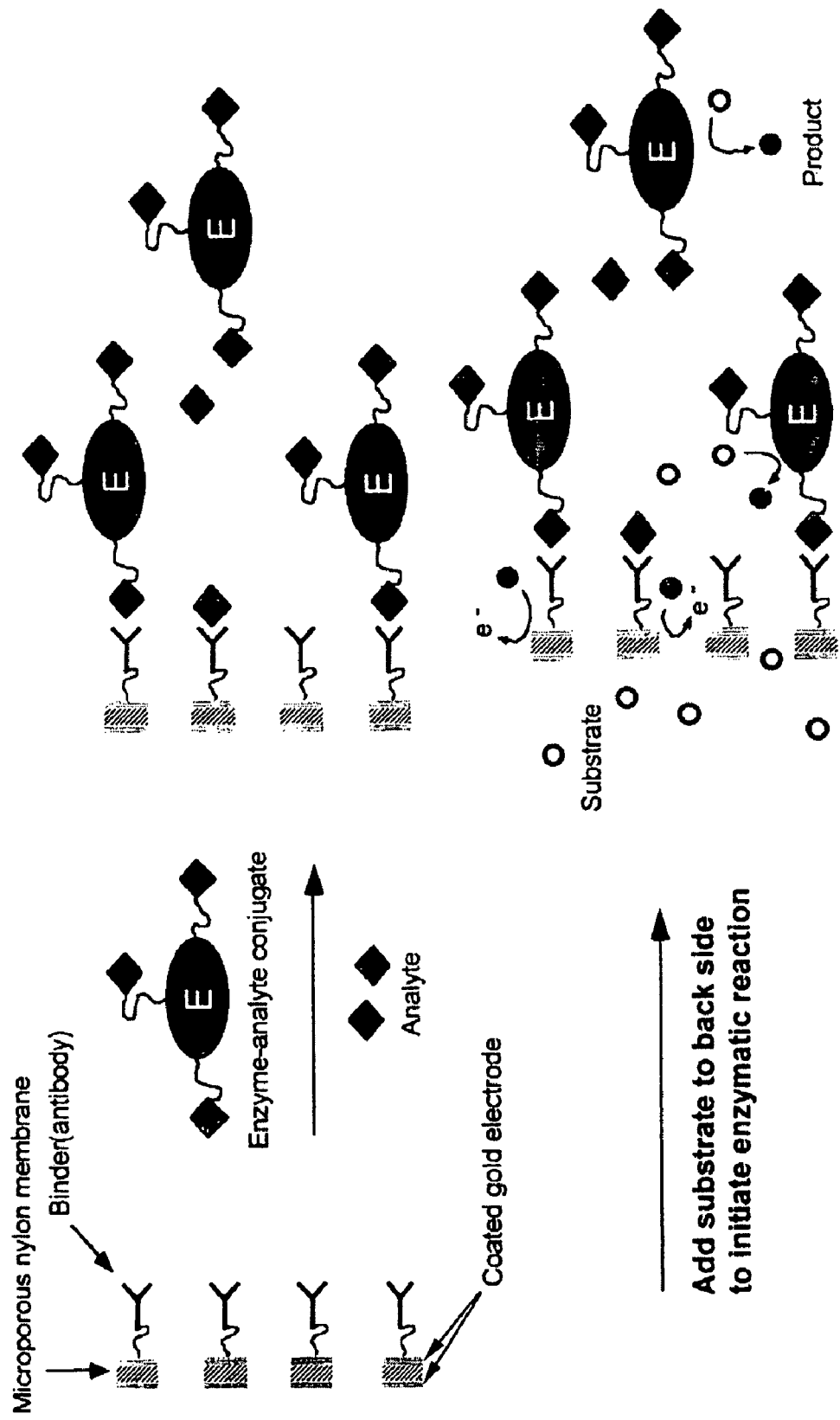
FIG. 8 is a diagram showing the principle and sequence of steps for the proposed separation-free immunoassay.

Referring to FIGS. 7a and 8, principles and sequence of steps for the proposed separation-free immunoassay are more fully described. A sample solution (for example, blood) containing an analyte is introduced into the biosensor through the hole (117) formed on the top cover (115). The introduced solution contacts the pad (114a) (for example, nitrocellulose membrane, paper, and glass fiber) in which a predetermined amount of an enzyme-analyte conjugate is absorbed. Then, the analyte protein and the enzyme-analyte conjugate dissolved in the solution form a competitive bonding to the biologically active material (antibody) immobilized on the working electrode (104). After sufficient binding has been formed, a substrate specific to the conjugated enzyme is introduced through the hole (118) formed on the bottom cover (116). The substrate passes through pores, contacts the bound enzyme-analyte conjugate, and initiates an enzymatic reaction. By this reaction, the substrate is transformed to the product, and the electrons transferred to the electrode generate an electrical signal. The electrical signal travels to the surface of the electrode system (102) and is detected by an appropriate device. The electrical signal may also be generated by the reaction of the substrate with the unbound enzyme-analyte conjugate. However, the unbound enzyme-analyte conjugate is sufficiently distanced from the surface of the electrode that the electrons generated from the enzyme-substrate reaction cannot reach the electrode. For this reason, washing steps and separation steps can be omitted.

The electrical signal is proportional to the quantity of captured enzyme-analyte conjugate, and the quantity of the analyte protein can therefore be quantitatively estimated from the calibration plot. Furthermore, since the counter electrode system (103) is formed on the opposite surface of the microporous membrane support (101), no additional electrode system is required. Therefore, a miniaturized and separation-free solid phase immunosensor can be achieved.

Figure 7B:
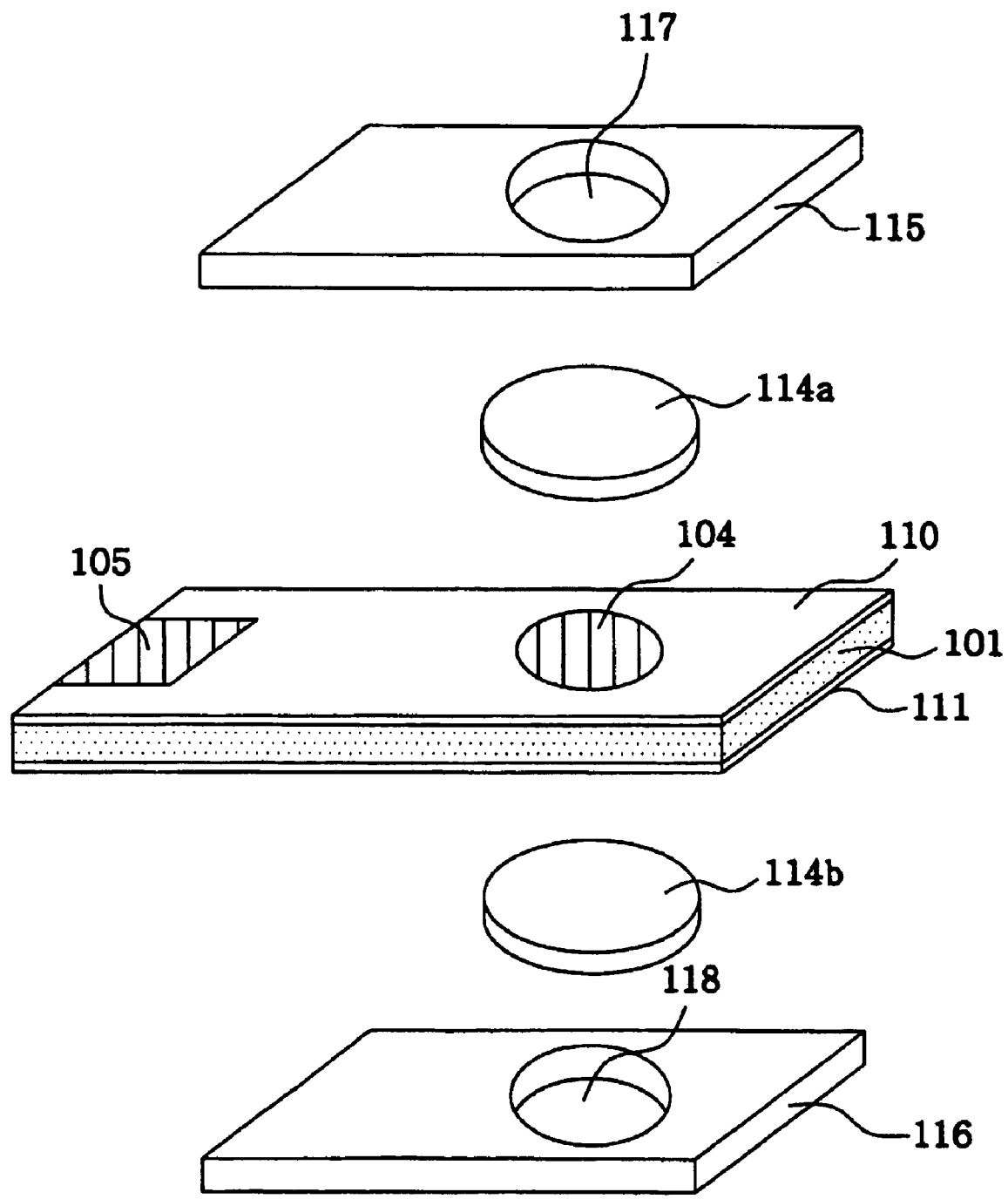
FIGS. 7b to 7e show various modifications of the biosensor, in accordance with the third embodiment of the present invention.
Figure 7C:
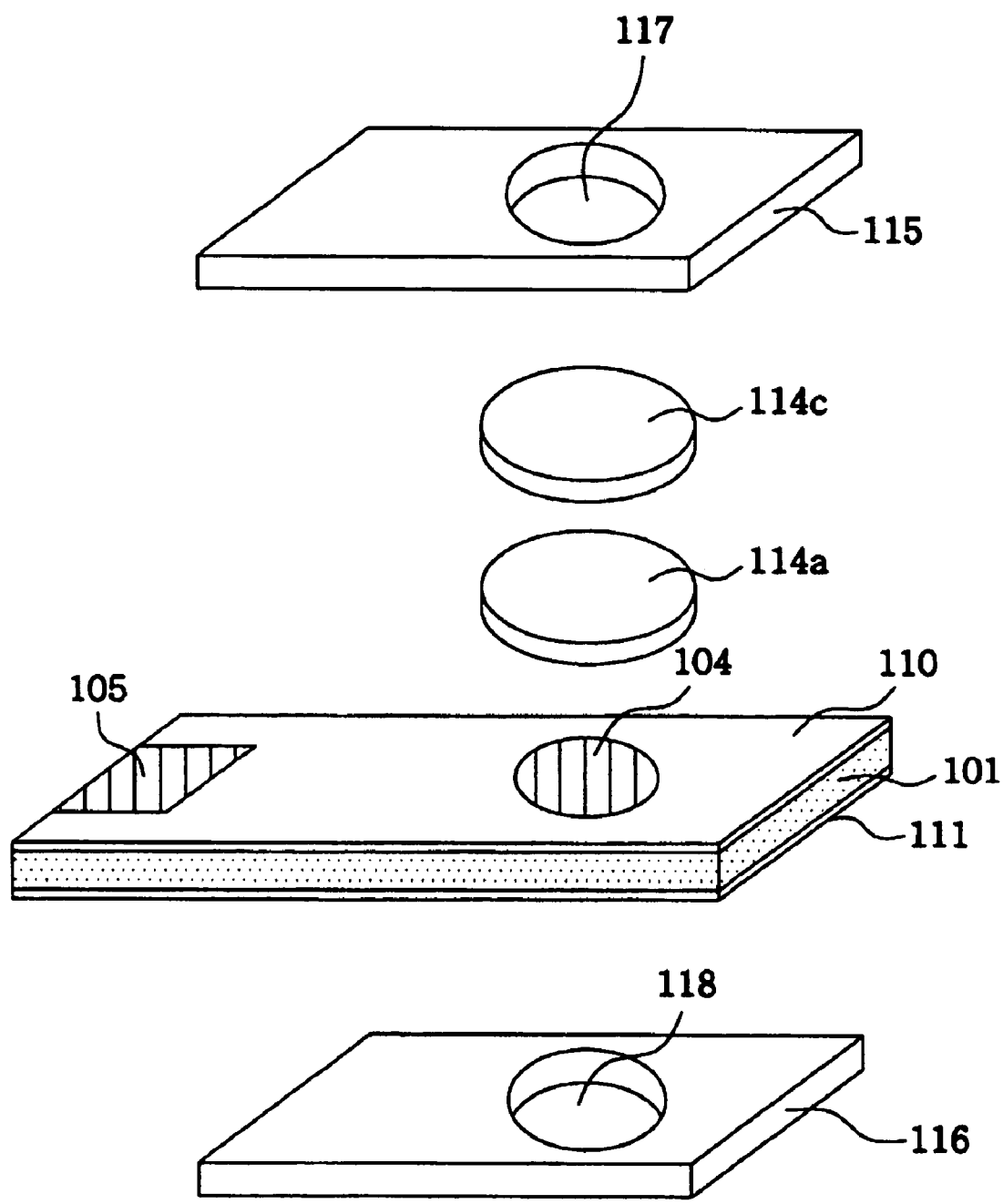
Figure 7D:
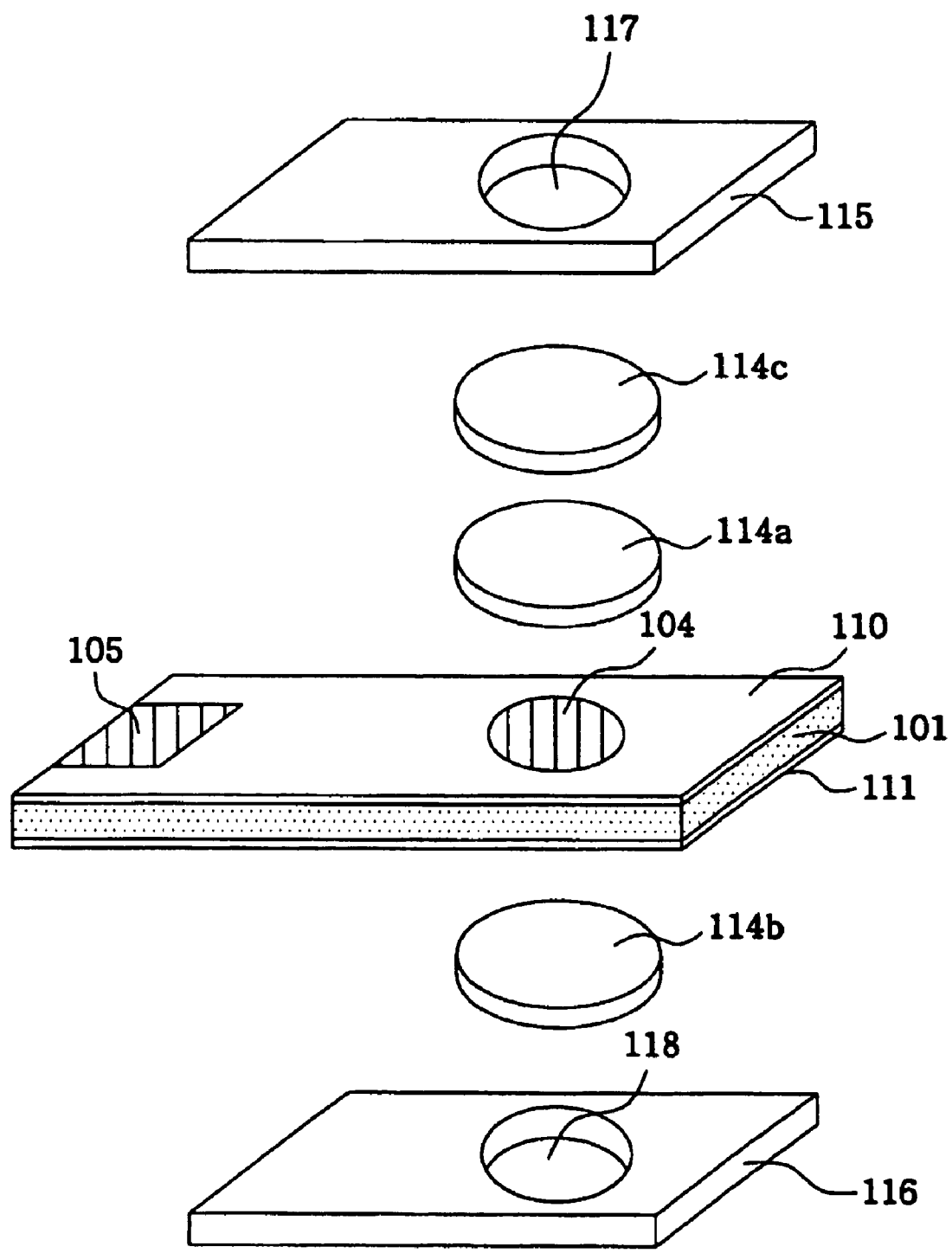
Figure 7E:
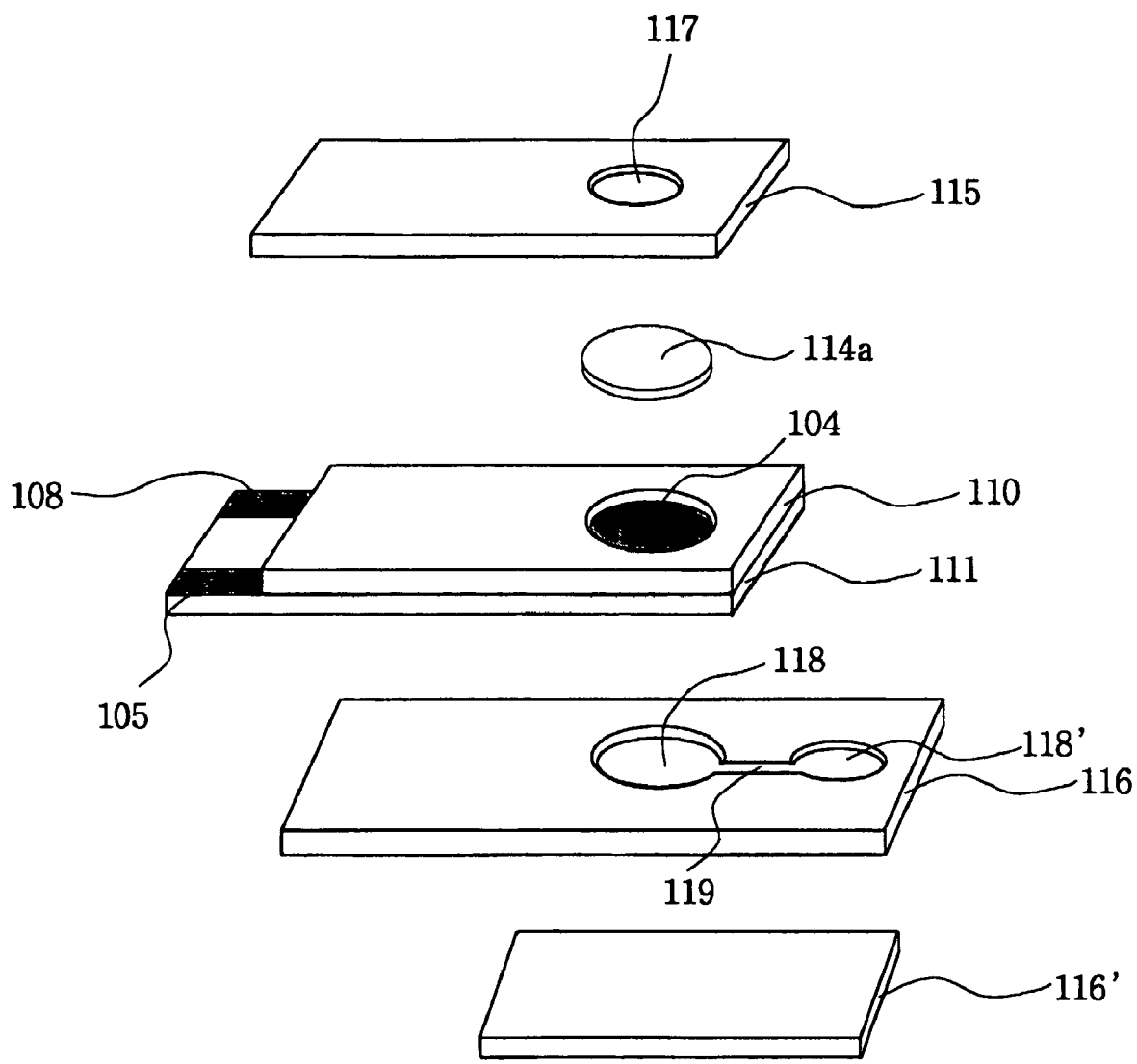

FIGS. 7b, 7c, 7d, and 7e each show other preferred embodiments with modified biosensor according to the present invention. As shown in FIGS. 7b and 7d, a pad (114b) on which substrate is absorbed may be added, which enables a simpler detection of the analyte protein. As shown in FIGS. 7c and 7d, a filter pad (114c) may be added, such that interferences such as solid particles (hematocrits) contained in human blood can be eliminated beforehand by, for example, size exclusion, charge exclusion, polarity phospholipid, and mixed control. Further, a protein stabilizer and/or a buffer solution can be absorbed on the filter pad (114c) to achieve improved detection for the analyte protein. As shown in FIG. 7e, a hole (117) through which a sample solution is added and a hole (118) connected via capillary to the substrate reservoir (118') through which a substrate solution is added can be formed on the same side, such that simpler provisions of the sample and substrate solutions can be achieved. A hole (118), connecting capillary (119) and a substrate reservoir (118') may be formed by punching or embossing the pattern on the bottom substrate (116). If the bottom substrate (116) is embossed to form the hole (118), connecting capillary (119), and the reservoir (118'), the second bottom plate is unnecessary.

As well known to a person skilled in the art, an enzyme-antibody conjugate, rather than the enzyme-analyte conjugate, may be absorbed into the pad (114a). Further, the choice of a suitable enzyme-substrate pair is also well known. For example, a uricase-uric acid pair, sarcosine oxidase-sarcosine pair, cholesterol oxidase-cholesterol pair, glycerol-3-phosphate oxidase-glycerol-3-phosphate pair, pyruvate oxidase-pyruvate pair, diaphorase-NADH pair, catalase-$H_2O_2$ pair, L-glutamate oxidase-L-glutamate pair, bilirubin oxidase-bilirubin pair, alkaline phosphatase-p-aminophenol phosphate pair, and glucose oxidase-glucose pair are all suitable enzyme-substrate pairs (see U.S. Pat. No. 5,830,680).

The biosensor according to the present invention can be also applied in a non-dried form.

Figure 9:
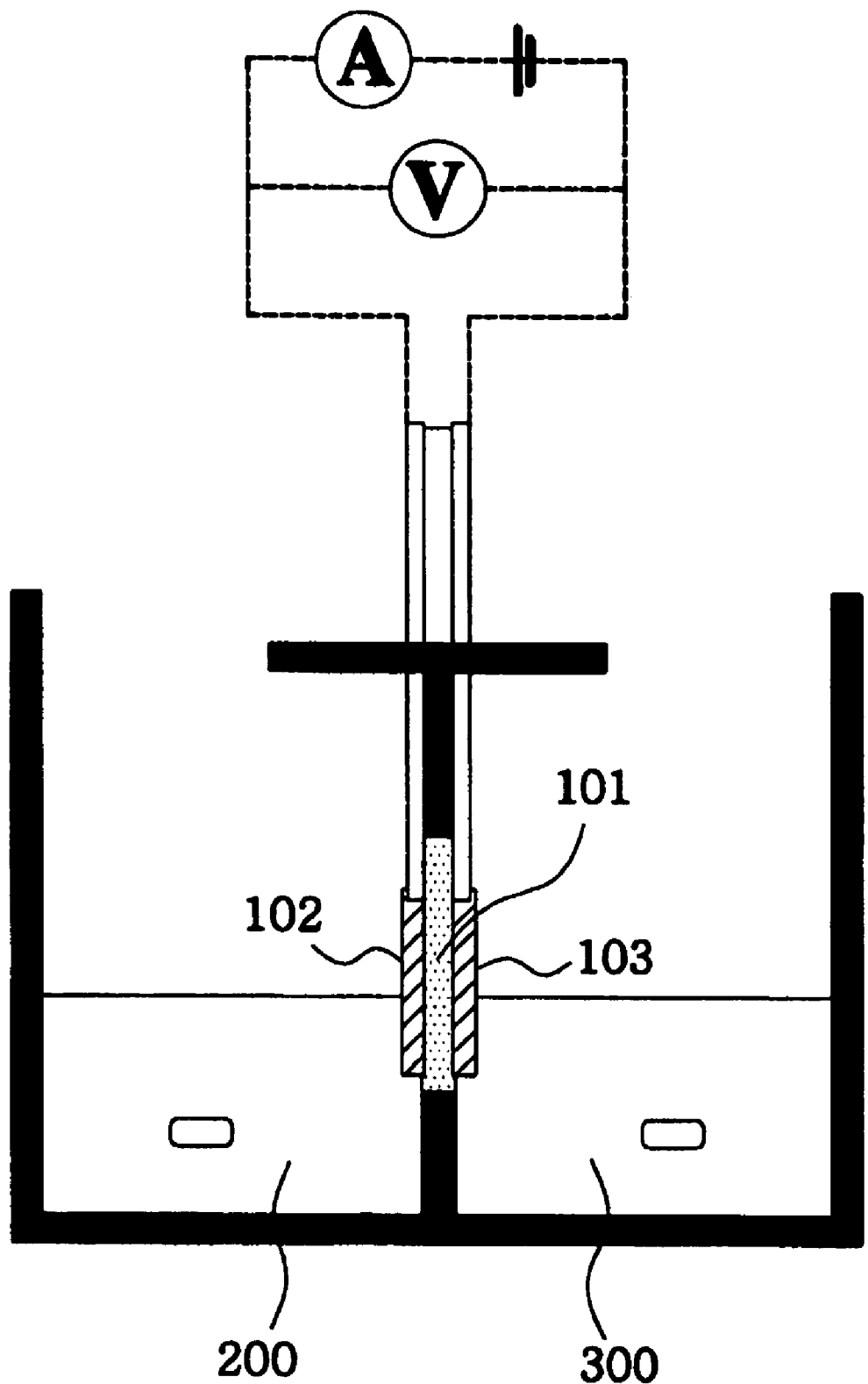
FIG. 9 is a schematic diagram of a diffusion cell arrangement of the present invention.

As shown in FIG. 9, a non-dried biosensor comprises: a microporous membrane support (101); a first electrode system (102) on which antibody is immobilized; a second electrode system (103); and a pair of insulating films, wherein the first electrode system (102) is formed on the surface of the microporous membrane support (101) and the second electrode system (103) is formed on the opposite surface of the microporous membrane support (101). An analyte and an enzyme-conjugate (an enzyme-analyte conjugate or an enzyme-antibody conjugate) are placed into a first chamber (200), and a substrate for the enzyme is placed into a second chamber (300).

As shown in FIG. 9, no additional electrode is required, because the first electrode system (102) and the second electrode system (103) are together formed on both surfaces of the microporous membrane support (101).

The biosensor of the present invention is applicable to any analyte capable of causing antibody production, for example, C-reactive protein, hCG, PSA, creatine phosphokinases (isozymes MB, BB, and MM), troponin, myoglobin, light-chain myosin, fibrinogen, thyroid stimulating hormone, FSH, hepatitis antigens, glycated proteins (such as Hb $A_{1c}$ and fructosamine) and various proteins associated with a wide variety of specific viruses such as the potato virus.

Substrate to be used depends on the enzyme employed. The skilled person would readily achieve suitable choice of enzyme-substrate pairs. For example, when glucose oxidase is used as an enzyme, the preferred substrate is glucose. Glucose oxidizes to gluconic acid and produces $H_2O_2$ by the catalytic action of glucose oxidase. The $H_2O_2$ generates an electrical signal at a potential (with respect to Ag/AgCl) of about +700 mV.

On the other hand, when alkaline phosphatase is used, p-aminophenyl phosphate is preferable. The p-aminophenyl phosphate produces by the action of alkaline phosphatase an electrically active species p-aminophenol is produced and further oxidized to generate optimum electrical signal at +190 mV (vs. Ag/AgCl) of applied potential.

Meanwhile, horseradish peroxidase uses $H_2O_2$ as a substrate, in which Fe(II) used as an electron transfer mediator oxidizes to Fe(III). The current produced by the reduction of Fe(II) can be detected by applying a reduction potential of −100 mV.

Physical adsorption or chemical bonding can achieve immobilization of the biologically active material on the working electrode, such as an enzyme, an electrode transfer mediator, or an antibody. Physical adsorption is achieved by dropping the biologically active material solution onto the working electrode, followed by culturing. This method utilizes the affinity between the biologically active material and the electrode forming material. Chemical bonding utilizes an activated self-assembled monolayer formed on the surface of the working electrode. Modification of the surface of the working electrode can be achieved by various methods using reactive compounds such as alkyl thiol, amine, and carboxylic acid. Covalent bonding of the biological active material to the self-assembled monolayer is formed (Meyerhoff et al., Mikrochim. Acta. 117/195-206, 1995).

A better understanding of the present invention may be obtained in light of the following examples, which are set forth to illustrate, but are not to be construed to limit the present invention.

Reagents

The sources of materials and reagents used were as follows:

glucose oxidase (GOx; EC 1.1.3.4, type VII-S, 245-900 units/g, from Aspergillus Niger; 2-[N-morpholino]ethanesulfonic acid (MES), 1-ethyl-3,3-dimethylaminopropyl carbodiimide (EDAC), N-hydroxysulfosuccinimide (NHS), potassium ferricyanide ($K_3Fe(CN)_6$), $\beta$-$_D$(+)-glucose, 2-mercaptoethylamine, and DL-6,8-thioctic acid amine, from Sigma (St. Louis, Mo., USA); 1,2-dithiolane-3-pentanoic acid, 3-mercaptopropionic acid, 11-mercaptoundecanoic acid, 16-Mercaptohexadecanoic acid (MHDA/C16), and ferroceneacetic acid (Fc—COOH), from Aldrich (Milwaukee, Wis., USA); disodium hydrogenphosphate and sodium dihydrogenphosphate, from Kanto Chemical (Tokyo, Japan); Nytran neutral microporous nylon membranes (0.2 μm pore size), from Schleicher and Schuell of Keene, N.H.; and nitrocellulose (NC) membranes from Whatman International (Maidstone, England). All other chemicals employed were of analytical grade.

Sample and standard solutions were prepared in a phosphate buffered saline (PBS, 140 mM NaCl). All aqueous solutions were prepared with deionized water (18MΩcm). Alkaline phosphatase (AKP), p-nitrophenyl phosphate, avidin (from egg white), biotin (vitamin H), and gelatin and bovine serum albumin (BSA) were purchased from Sigma of St. Louis, Mo. p-Aminophenyl phosphate was synthesized from p-nitrophenyl phosphate. Deionized water used in the preparation of buffer solution was Yamato Millipore WQ 500, (resistance: 18MΩ).

EXAMPLE 1

1-1) Fabrication of Symmetric Double-Sided Microporous Gold Electrodes

The microporous nylon membranes (15×30 mm$^2$) were put under an appropriate mask having a 6 mm diameter and a 13 mm-wide outlet strip (for electrical connection purposes). Using physical vapor deposition technique, the membranes were coated on both surfaces with gold; sputtering time 300 s, pressure 75 mTorr, plasma current 25-30 mA, potential 350-500 V. This yielded a disk-shaped gold electrode at the center of the membrane with an outer diameter of 4 mm and a thickness of approximately 300 Å. A layer of PVC (33% PVC and 67% bis(2-ethylhexyl)sebacate (all w/w %), dissolved in tetrahydrofuran(THF) (1:6 w/v), was cast around the center disk electrode, including over the narrow gold lead outlet. This left the 6 mm disc-shaped gold electrode untouched in the center. The shape of the electrode is depicted in FIG. 2a. In another embodiment, gold is coated on the both sides of a nylon membrane (6×6 cm$^2$) without a mask and cut in the shape as depicted in FIG. 2a. The piece of gold-coated electrode, then, was placed between the two insulating films with screen-printed electrode connectors and pressed to assemble the symmetric double-sided microporous electrodes.

1-2) Fabrication of Asymmetric Double-Sided Microporous Gold Electrode

Figure 2E:
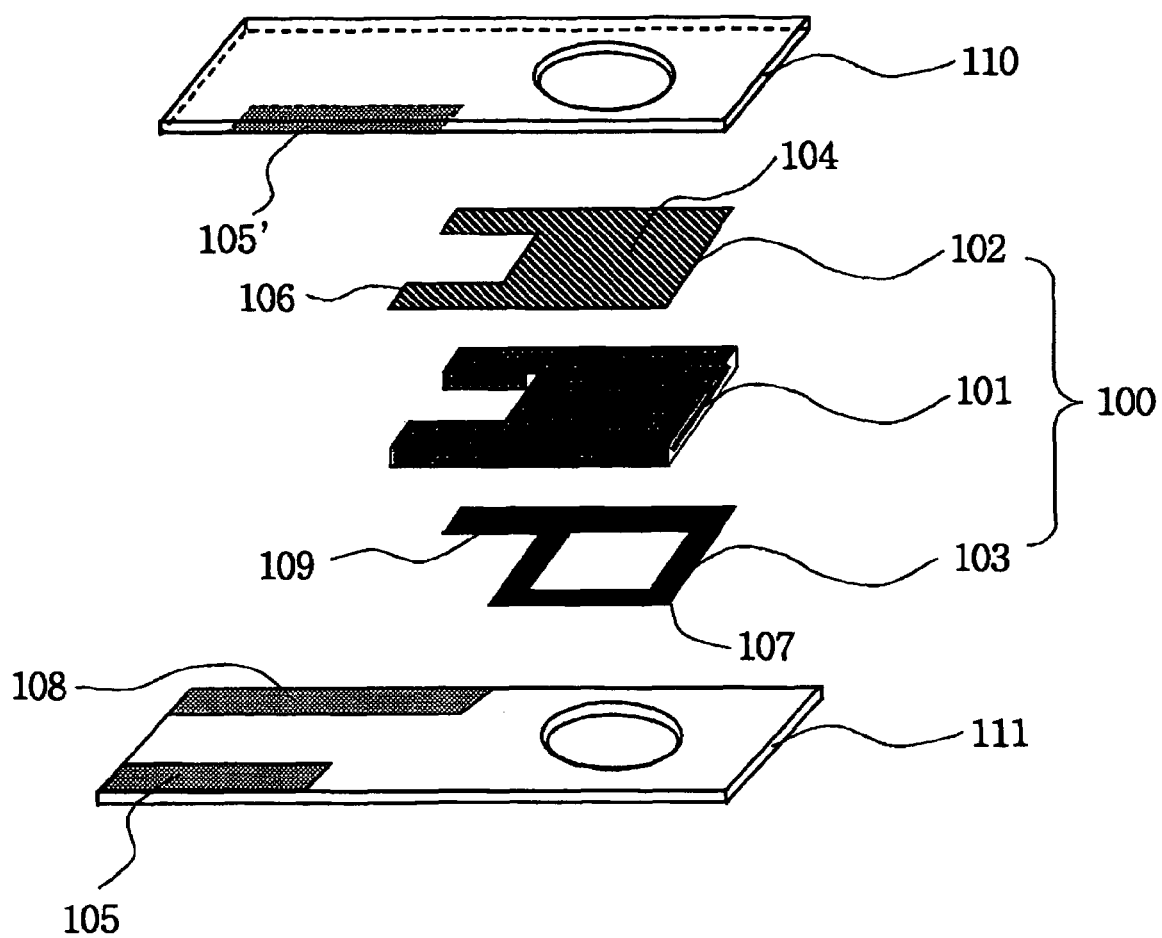
FIG. 2e is an exploded perspective view of an asymmetric microporous electrode-based biosensor, in which modification of the biosensor, with electrical connectors separately formed on two insulating substrates in accordance with a first embodiment of the present invention.
Figure 2F:
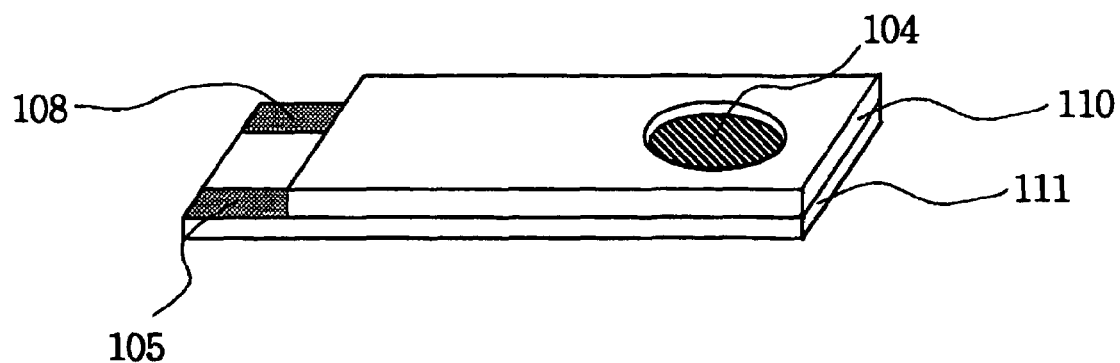
FIG. 2f is a perspective view of the biosensor of 2e, in which modification of the biosensor, in accordance with a first embodiment of the present invention.
Figure 10:
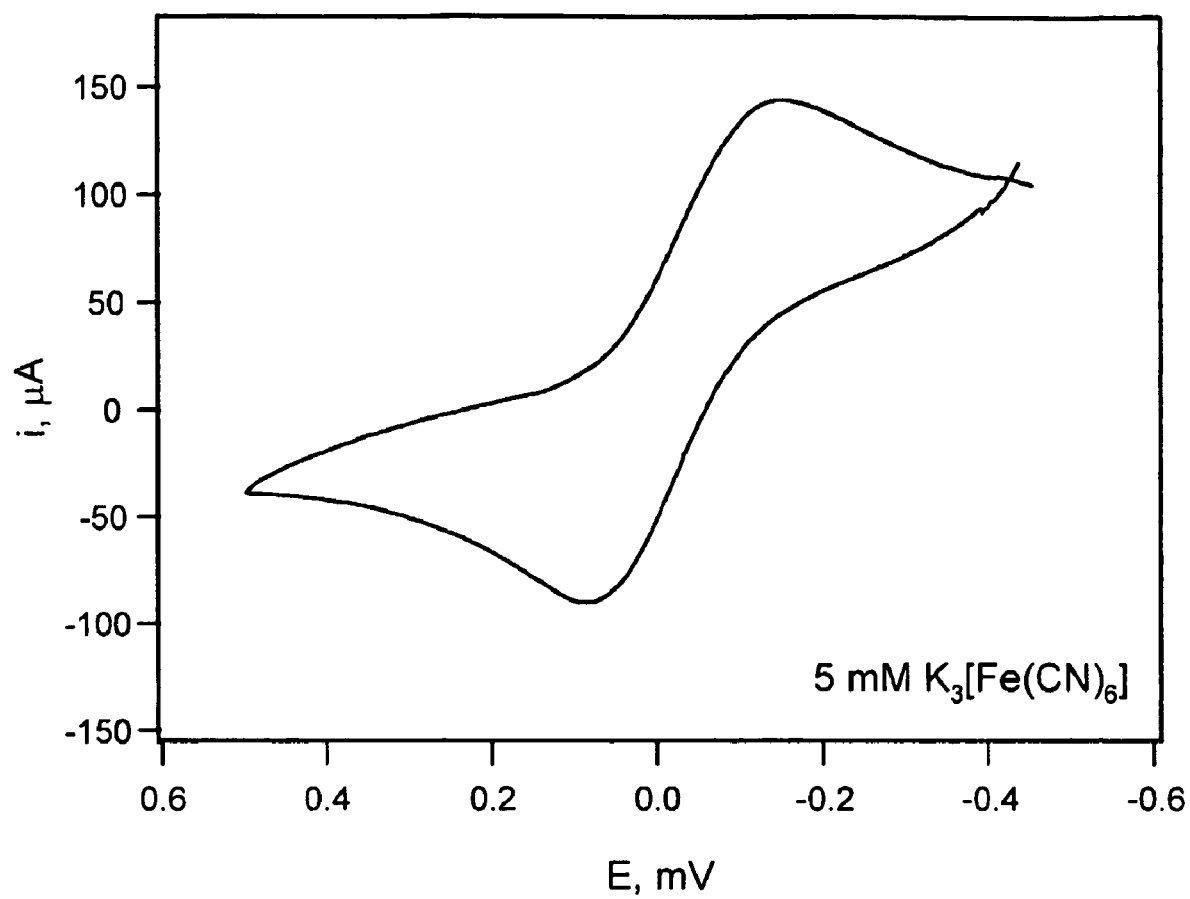
FIG. 10 is a cyclic voltammogram of the biosensor, an asymmetric microporous electrode-based biosensor in Example 1, in which potassium ferricyanide is used as a redox agent for the electrode.

Counter electrode, which was patterned to the contour line of the working electrode with hollow center, was screen-printed with carbon paste (or any conducting paste such as silver/silver chloride) on one side of the nylon membrane. On the opposite side of the membrane, gold electrode was formed by physical deposition method as described in Example 1-1. The electrode was cut in the shape as shown in FIG. 2e, and pressed between the two insulating films with screen-printed electrode connectors. The electrochemical characteristics of the asymmetric double-sided microporous electrodes was examined in a Fe(III)/Fe(II) containing buffer solution using cyclic voltammogram (scan rate: 60 mV/min); as shown in FIG. 10, the electrode provides reversible response with no indication of short-circuit between the deposited gold and screen-printed carbon.

1-3) Immobilization of Biologically Active Material

The electrodes were rinsed with the MES buffer and immediately placed in 10 μg of stirred phosphate buffer containing 10 mg/ml GOx and 140 mM NaCl at pH 7.4 for one hour, allowing physical adsorption of the GOx on the surface of the gold electrode, after which they were rinsed with phosphate buffer.

1-4) Fabrication of a Glucose Sensor

The self-sampling-and-flow glucose sensor shown in FIGS. 4a and 4b was fabricated by sandwiching the microporous gold strip electrode between a porous nitrocellulose (NC) strip and a glass fiber as an absorption pad.

1-5) Analytical Performance of the Glucose Sensor

Figure 11:
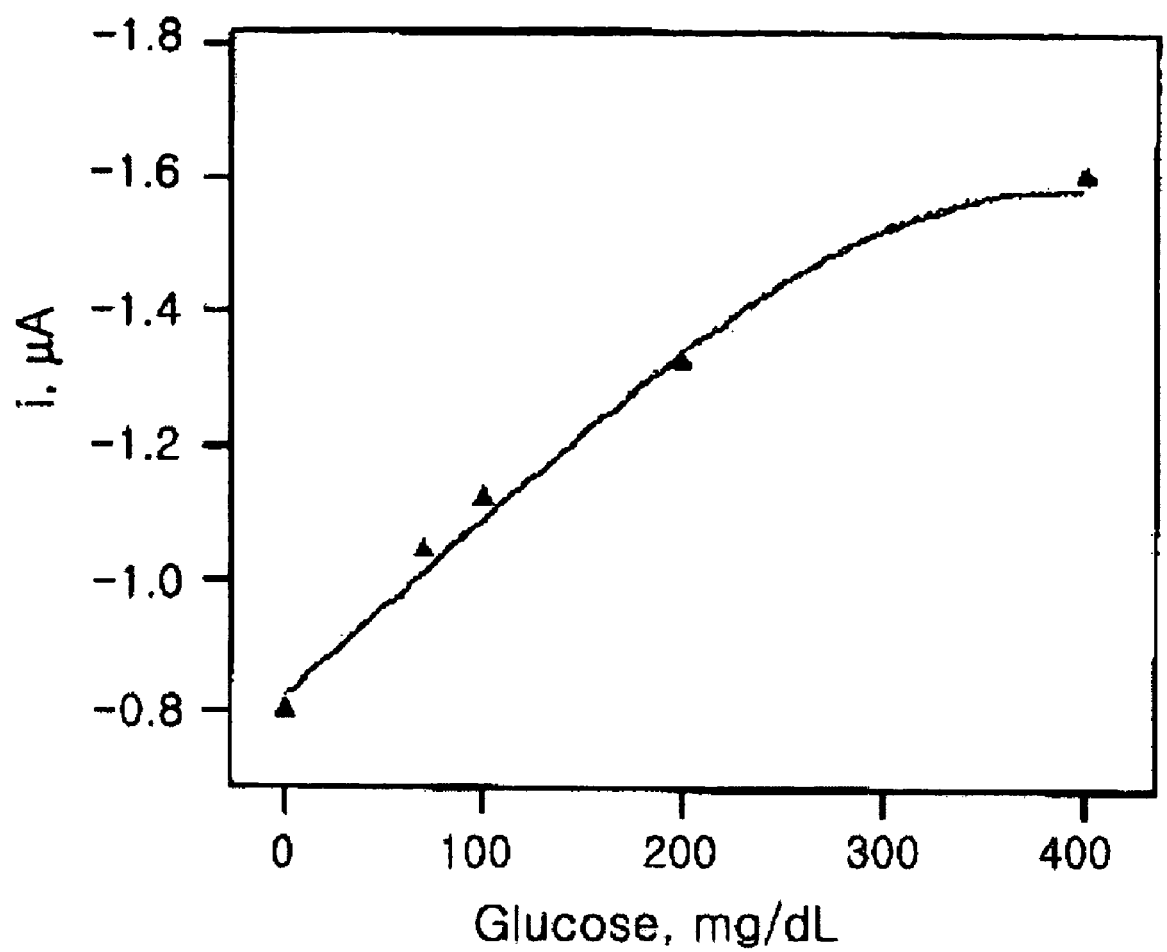
FIG. 11 is a typical calibration curve of the biosensor of Example 1 in which glucose oxidase is physically immobilized on the working electrode for a glucose analysis.

In order to test an analytical performance of the glucose sensor, the steady-state response to glucose was measured by an amperometric technique, with a standard glucose solution. FIG. 11 shows a typical calibration curve of the biosensor at a potential of 0.8V, revealing that the glucose sensor could respond to glucose for about thirty minutes. A linear response was observed in the range of 0 mg/dL to 200 mg/dL glucose. The slope was $2.60 \times 10^{-3}$ nA/(mg/dL) and the correlation coefficient was 0.988. From these results, it was confirmed the continuous self-sampling and detection is possible with the biosensor of present invention.

EXAMPLE 2

2-1) Fabrication of Gold Electrode

The gold electrode was obtained in the same manner as described in Example 1-1.

2-2) Immobilization of Biologically Active Materials

The electrode was rinsed with the MES buffer and immediately placed in a stirred 10 µl of phosphate buffer containing 10 mg/ml Gox, 200 mM potassium ferricyanide, and 140 mM NaCl at pH 7.4 for one hour, after which they were rinsed with phosphate buffer.

2-3) Fabrication of a Glucose Sensor

The self-sampling-and-flow gluxose sensor was fabricated by sandwiching the microporous gold strip electrode between a porous NC strip and a glass fiber as an absorption pad.

2-4) Analytical Performance of the Glucose Sensor

Figure 12:
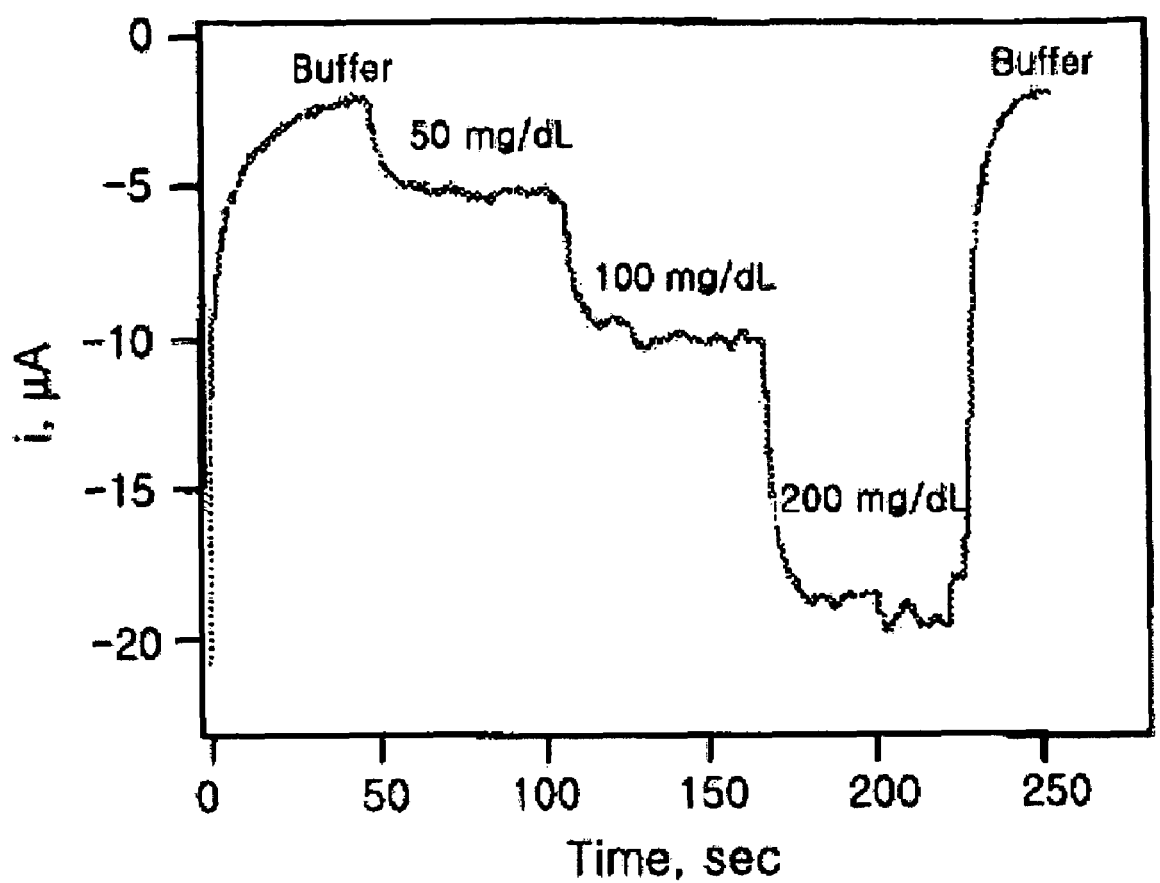
FIG. 12 is a dynamic response curve of the biosensor of Example 2, in which glucose oxidase and potassium ferricyanide are physically immobilized on the working electrode.

In order to test an analytical performance of the glucose sensor, the steady-state response to glucose was measured by amperometric technique. FIG. 12 showed a dynamic response of the biosensor at a potential of 0.38V, revealing that the glucose sensor could respond to each of glucose solutions (50 mg/dL, 100 mg/dL, and 200 mg/dL) for one hour. FIG. 12 showed the typical dynamic response curve for the glucose analysis. A linear response was observed in the range of 0 mg/dL to 200 mg/dL glucose. The slope was 85.8 nA/(mg/dL) and the correlation coefficient was 0.998. These results showed that more sensitive response to the glucose could be obtained even at a low potential of 0.38V. From these results, it was confirmed the continuous self-sampling and detection is possible with the biosensor of present invention.

EXAMPLE 3

A separation-free, solid phase immunosensor as illustrated in FIG. 7a was prepared.

3-1) Fabrication of Gold Electrode

The gold electrode was obtained in the same manner described in Example 1-1.

3-2) Fabrication of a Biosensor

The electrode was rinsed with the MES buffer. 10 µl of phosphate buffer containing 0.05 mg/ml avidin and 0.05 M sodium carbonate at pH 9.6 was dropped on the working electrode. Then, the electrode was cultured at 4° C. for sixteen hours. As a pad (114a), glass fiber membrane (Whatman International of Maidstone, England) on which 50 µl of glucose oxidase-biotin conjugate (2.5 µg/ml) was absorbed, was used.

3-3) Calibration

Figure 13:
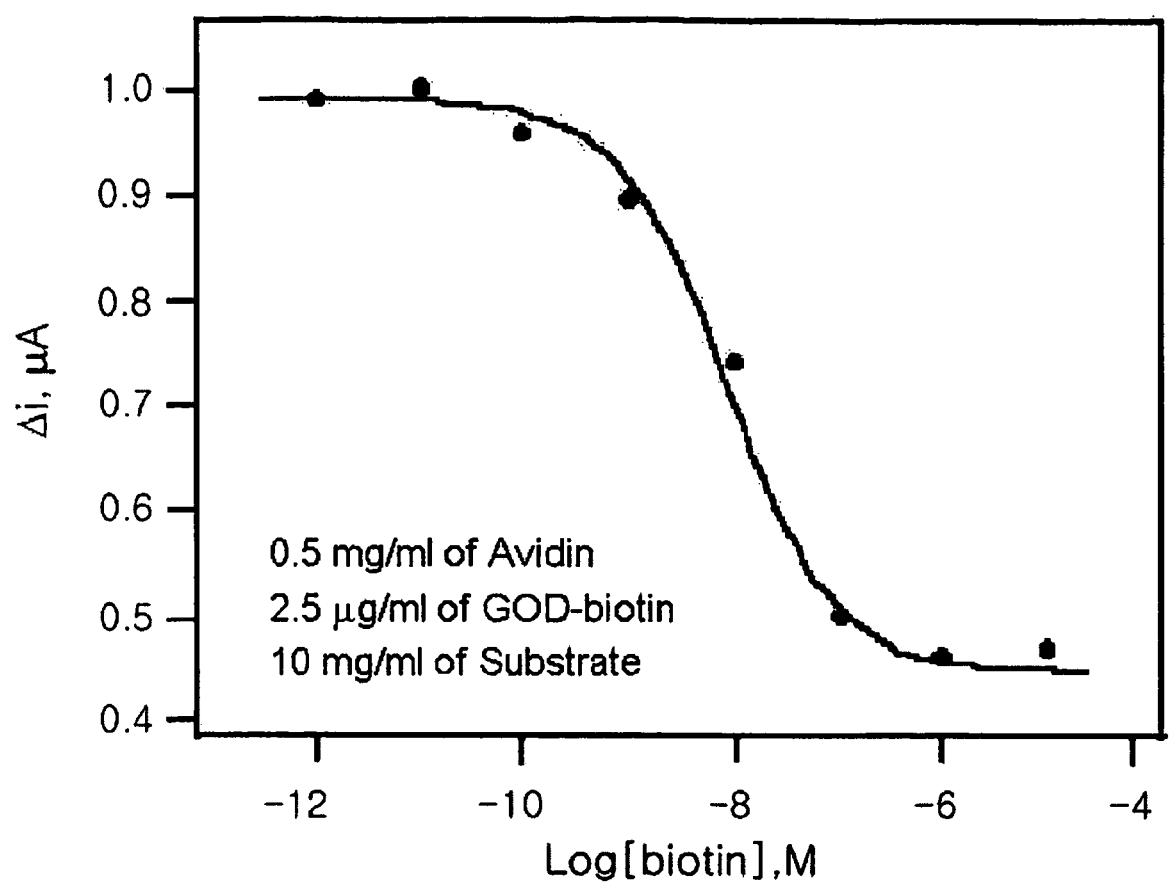
FIG. 13 is a calibration curve of the biosensor of Example 3 in which glucose oxidase-biotin conjugate is used as an enzyme-analyte conjugate and avidin is used as an antibody.

With the immunosensor obtained from Example 3-2, calibration was performed: Standard biotin solutions were diluted to the concentrations of $10^{-5}$M to $10^{-14}$M. Each of the standard solutions was added to the immunosensor through a hole (117) formed on the top cover (115). Stabilization of the competitive binding between avidin and biotin or the enzyme conjugate was achieved at an applied potential of +800 mV. Then, substrate (glucose) was added through a hole (118) formed on the bottom cover (116). The current generated by an enzymatic reaction was measured. FIG. 13 showed a calibration curve in which a current change depends on the concentration of biotin. A prominent signal difference was found between $10^{-7}$ M (1.0 µA) and $10^{-10}$ M (0.5 µA) biotin.

3-4) Measurement of Signal Change

With the immunosensor obtained from Example 3-2, the dynamic response curve was obtained: $10^{-12}$M of biotin buffer solution and $10^{-4}$M of biotin-free buffer solution was added to the immunosensor, respectively. After the sensor reached stabilization, 10 µl of a glucose solution was added at the backside of the sensor through the hole (118). The dynamic response of the immunosensor was measured by an amperometric technique, and the results thereof are shown in FIG. 14.

Figure 14:
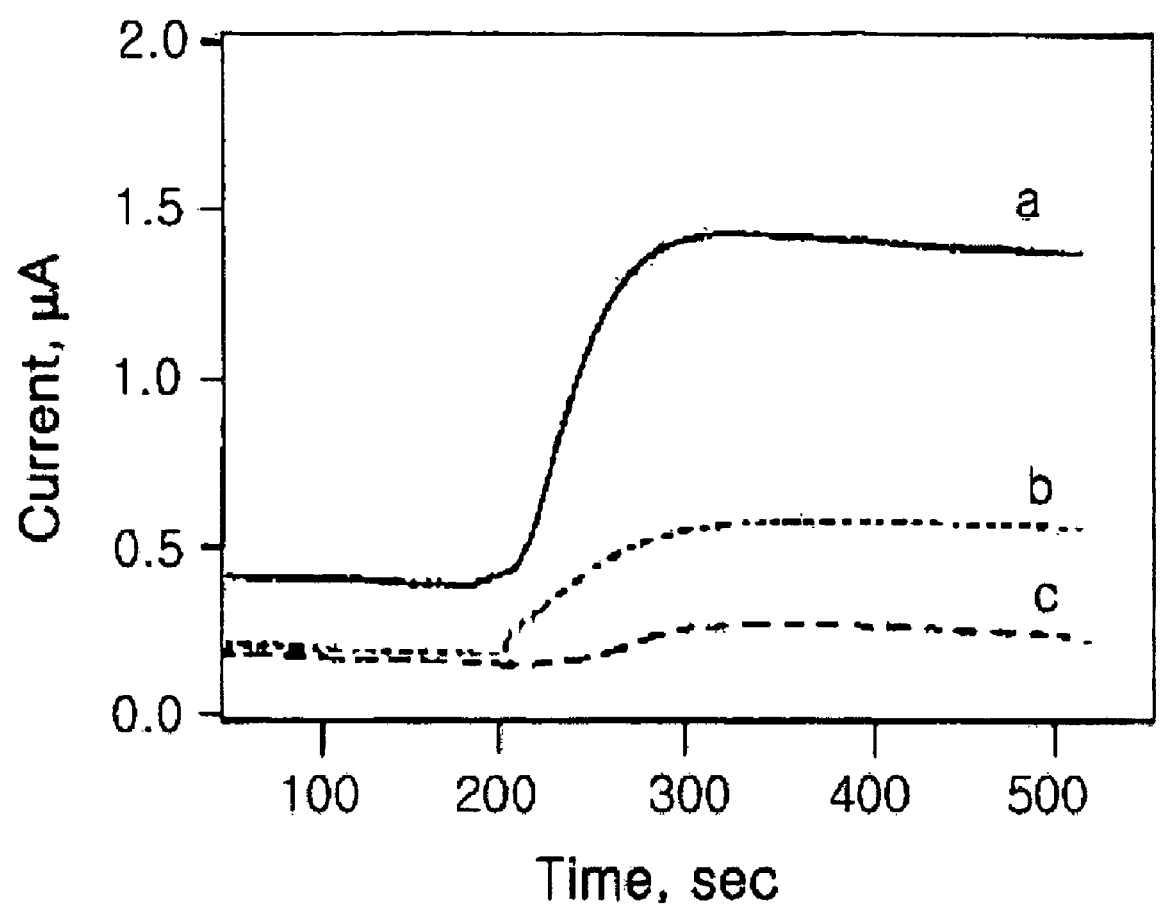
FIG. 14 is a dynamic response curve of the biosensor of Example 3.

FIG. 14 indicated that the current change for $10^{-12}$M of biotin buffer solutions was 1 µA, and the current change for $10^{-4}$ M of biotin buffer solutions was 0.4 µA. The current change for biotin-free buffer solution was about 0.05 µA. From these results, it was confirmed that this model immunosensor could be modified for the detection of suitable antigen-antibody reactions.

EXAMPLE 4

A separation-free, solid phase C-Reactive Protein (CRP) immunosensor was prepared in the format shown in FIG. 7e, and similar biomaterial immobilization method as described in Examples 3-1 and 3-2; anti-CRP (0.0125 mg/mL) was immobilized on the gold electrode by physical adsorption, alkaline phosphatase (ALP) was used as the linked enzyme to CRP (ALP-CRP; 0.2 mg/mL) instead of the glucose oxidase-biotin of Example 3-1, and p-aminophenyl phosphate (5 mg/mL) was used instead of the glucose of Example 3-2. Standard CRP solutions were prepared by dissolving known amount of CRP in the reconstituted serum and added to the hole (117) of the biosensor shown in FIG. 7e. The substrate p-Aminophenol was added to the hole 118, which traveled through the capillary 119 to the reservoir 118', and diffused through the micro pores of the electrode system 100 (FIG. 7e) to result in electrochemical signal. The current response of the immunosensor was measured by an amperometric technique at an applied potential of +150 mV, and the results thereof are summarized in FIG. 15.

Figure 15:
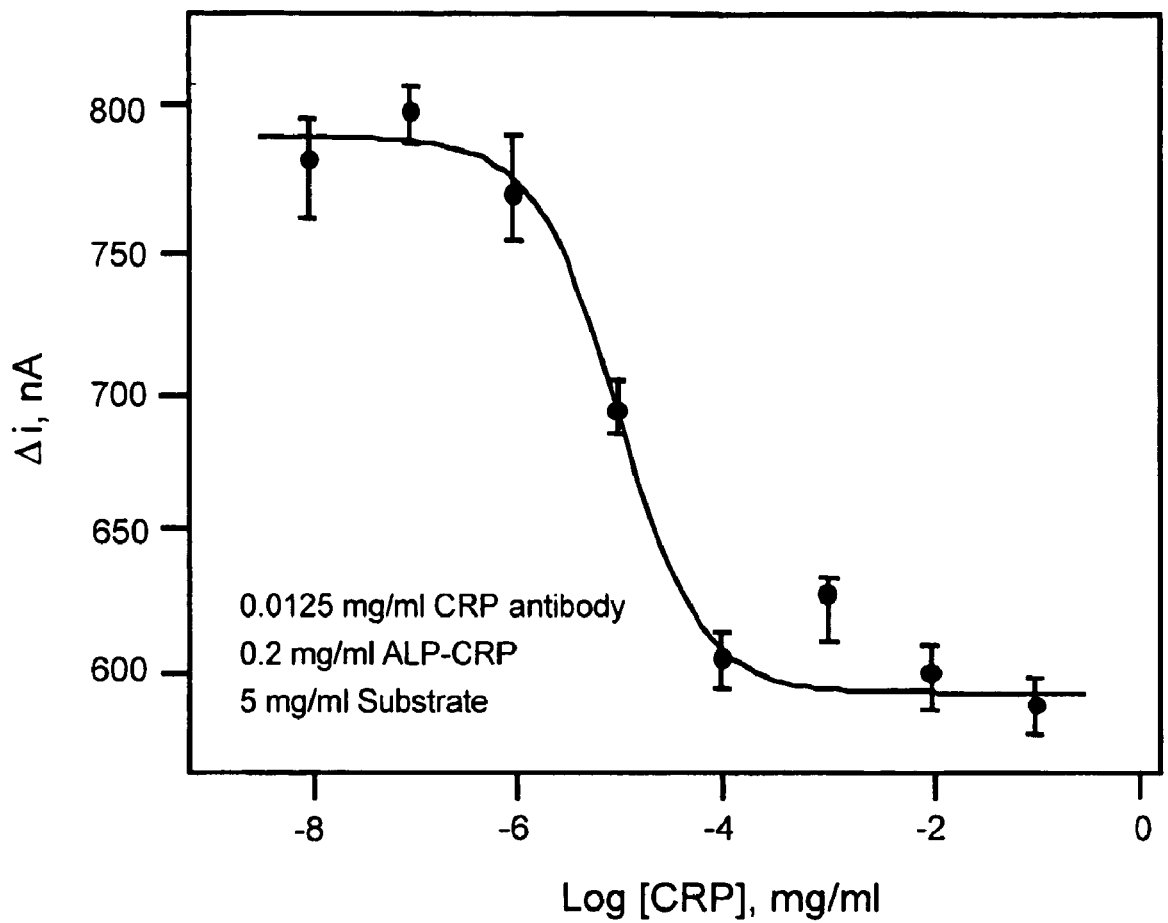
FIG. 15 is a calibration curve of the CRP biosensor of Example 4; the CRP antibody immobilized on the front microporous electrode, alkaline phosphatase-CRP conjugate dried in the upper pad, and p-aminophenyl phosphate soaked through the bottom pad are used to obtain the signal.

As shown in FIG. 15, the current change for $10^{-6}$ mg/mL of CRP/serum solution was 0.75 µA, and the current change for $10^{-4}$ mg/mL of CRP/serum solution was 0.6 µA. From these results, it was confirmed that the immunosensor could be effectively used in highly sensitive detection of CRP.

What is claimed is:

1. A biosensor for separation-free enzyme immunoassays without washing, comprising:
   a microporous membrane support;
   a first electrode system consisting of a working electrode on which antibodies are immobilized, a first electrode connector, and a first lead outlet;
   a second electrode system consisting of a counter electrode, a second electrode connector and a second lead outlet;
   a pair of insulating films, covering surfaces of the first and second electrode systems except for the areas of the working electrode, the first electrode connector, the counter electrode and the second electrode connector; and
   a pad containing an enzyme-antibody conjugate on the top of the working electrode, and
   a pair of covers consisting of an upper cover having a hole and a lower cover having a hole,
   wherein, the first electrode system is formed on the surface of the microporous membrane support and the second electrode system is formed on the opposite surface of the microporous membrane support, wherein, the working electrode and the counter electrode are formed directly on the microporous membrane support, whereby the electrodes being microporous and allowing a sample liquid to pass through the surface of the working electrode to the surface of the counter electrode and a substrate to pass through the surface of the counter electrode to the surface of the working electrode, wherein a sample solution containing an analyte, introduced into the hole of the upper cover, reacts to form a bound enzyme-antibody conjugate with the antibodies and an unbound enzyme-antibody conjugate, the bound enzyme-antibody conjugate being formed in the working electrode, and wherein the substrate participates in the enzyme reaction with the enzyme from the bound enzyme-antibody conjugate to generate electrons transferable to the electrode and the unbound enzyme-antibody conjugate to generate electrons not transferable to the electrode.

2. The biosensor as set forth in claim 1, wherein the counter electrode is made of an electrically conductive material symmetrically to the working electrode.

3. The biosensor as set forth in claim 2, wherein the electrically conductive material is selected from the group consisting of gold, platinum, silver, silver chloride, rhodium, iridium, ruthenium, palladium, osmium, carbon, copper, and mixtures thereof.

4. The biosensor as set forth in claim 1, wherein the counter electrode is made of an electrically conductive material asymmetrically to the working electrode.

5. The biosensors as set forth in claim 2 or 4, wherein the first and second insulating films contain separately formed electrical connectors, and wherein the symmetric or asymmetric double-sided electrodes are sandwiched between the insulating films and connected to the connectors of insulating films.

6. The biosensor as set forth in claim 1, wherein the first and second lead outlets and connectors are separated from each other.

7. The biosensor as set forth in claim 1, the microporous membrane support is made of a member selected from the group consisting of an organic polymer, inorganic polymer, natural fabrics or synthetic fibers, papers and ceramics.

8. The biosensor as set forth in claim 1, wherein the microporous membrane support is a microporous nylon mesh.

9. The biosensor as set forth in claim 1, further comprising a pad containing the substrate below the counter electrode.

10. The biosensor as set forth in claims 1 or 9, further comprising a filter pad between the pad on the top of the working electrode and the upper cover.

11. The biosensor as set forth in claim 10, wherein the filter pad contains a protein stabilizer or a buffer solution or a mixture thereof.

12. The biosensors as set forth in claims 1, wherein a reservoir formed in the lower cover, and connected via capillary with the hole of the lower cover.

13. The biosensor as set forth in claim 1, wherein the conjugated enzyme is selected from any reductase or oxidase enzymes.

* * * * *